US008321135B2

(12) United States Patent  
Fender et al.

(10) Patent No.: US 8,321,135 B2  
(45) Date of Patent: Nov. 27, 2012

(54) METHOD AND APPARATUS FOR PREDICTING SOYBEAN SEED RESISTANCE BASED ON NEAR-INFRARED SPECTROSCOPY

(75) Inventors: Christopher M. Fender, Columbia, MO (US); David A. Sleper, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 620 days.

(21) Appl. No.: 10/079,468

(22) Filed: Feb. 19, 2002

(65) Prior Publication Data

US 2003/0177525 A1  Sep. 18, 2003

Related U.S. Application Data

(60) Provisional application No. 60/269,474, filed on Feb. 16, 2001.

(51) Int. Cl.
*G01N 33/48* (2006.01)
*G06F 19/00* (2006.01)
*C12Q 1/68* (2006.01)

(52) U.S. Cl. ................................. 702/19; 702/20; 435/6
(58) Field of Classification Search .................... 703/11; 702/19; 435/4
See application file for complete search history.

(56) References Cited

U.S. PATENT DOCUMENTS

| 5,491,081 A | 2/1996 | Webb | |
| 6,214,550 B1 * | 4/2001 | Malins | 435/6 |
| 2003/0028914 A1 * | 2/2003 | Liu et al. | 800/278 |

FOREIGN PATENT DOCUMENTS

WO  WO0071993  11/2000

OTHER PUBLICATIONS

U.S. Appl. No. 60/201,245.*
Qiu et al., Theor. Appl. Genet., vol. 98, pp. 356-364, 1999.*
Borggaard et al., Anal. Chem. 1992, 64:545-551.*
Discriminant Function Analysis, www.statsoft.com/textbook/stdiscan.html, Copyright 1984.*
Bewig et al., JAOCS, 1994, vol. 71, No. 2, p. 195-200.*
Robinson et al., Revue Nematol., 1988, vol. 11, No. 1, p. 99-107.*
Rutherford, Journal of Chemical Ecology, 1998, vol. 24, No. 9, p. 1447-1463.*
Marek et al., Crop Sci., 2000, vol. 40, p. 713-716.*
Yuhara (Res. Bull. Hokkaido National Agricultural Experiment Station, 1975, No. 111, p. 91-100; Japenese Translation Document).*
Bewig, Karen Marie, "Discriminant Analysis of Vegetable Oils Using Near Infrared Reflectance Spectroscopy," A Thesis Presented to the Faculty of the Graduate School University of Missouri-Columbia, Dec. 1992, Chapter 1, pp. 1-3.

Buss, G.R., H.M. Camper, Jr., and C.W. Roane (2), "Registration of Hutcheson Soybean," Crop Science, vol. 28, Nov.-Dec. 1988, p. 1024.
Delwiche, Stephen R., Robert A. Graybosch, and C. James Peterson, "Identification of Wheat Lines Possessing the 1AL.1RS or 1BL.1RS Wheat-Rye Translocation by Near-Infrared Reflectance Spectroscopy," American Association of Cereal Chemists, Inc., vol. 76, No. 2, 1999, pp. 255-260.
Endo, Burton Y., "Penetration and Development of Heterodera glycines in Soybean Roots and Related Anatomical Changes," Phytopathology, vol. 54, Jan. 1964, pp. 79-88.
Golden, A.M., J.M. Epps, R.D. Riggs, L.A. Duclos, J.A. Fox, and R.L. Bernard, "Terminology and Identity of Infraspecific Forms of the Soybean Cyst Nematode (Heterodera Clycines)," Plant Disease Reporter, vol. 54, No. 7, Jul. 1970, pp. 544-546.
Nickell, C.D., D.J. Thomas, T.R. Cary, and D. Heavner(4), "Registration of 'Macon' Soybean," Crop Science, vol. 36, Sep.-Oct. 1996, p. 1410.
Nickell, C.D., D.J. Thomas, and P. Stephens(2), "Registration of 'Hamilton' Soybean," Crop Science, vol. 30, Nov.-Dec. 1990, p. 1364.
Nilsson, M., T. Elmqvist, and U. Carlsson, "Use of Naar-Infrared Reflectance Spectrometry and Multivariate Data Analysis to Detect Anther Smut Disease (*Microbotryum violaceum*) in Silene dioica," Phytopathology, vol. 84, No. 7,1994, pp. 764-770.
Giu, J., J. Hallmann, N. Kokalis-Burelle, D.B. Weaver, R. Rodriguez-Kabana, and S. Tuzun, "Activity and Differential Induction of Chitinase Isozymes in Soybean Cultivars Resistant or Susceptible to Root-knot Nematodes," Journal of Nematology, vol. 29, No. 4, Dec. 1997, pp. 523-530.
Rao-Arelli A.P., K.W. Matson, and S.C. Anand, "A Rapid Method for Inoculating Soybean Seedings with Heterodera glycines," Plant Disease, vol. 75, No. 6, Jun. 1991, pp. 594-595.
Roberts, C.A., K.J. Moore, D.W. Graffis, H.W. Kirby, and R.P. Walgenbach, "Quantification of Mold in Hay by Near Infrared Reflectance Spectroscopy," Dairy Science, vol. 70, 1987, pp. 2560-2564.
Roberts, C.A., R.E. Joost, and G.E. Rottinghaus, "Quantification of Ergovaline in Tall Rescue by Near Infrared Reflectance Spectroscopy," Crop Science, vol. 37, No. 1, Jan.-Feb. 1997, pp. 281-284.
Ross, J.P., "Physiological Strains of Heterodera Glycines," Plant Disease Reporter, vol. 46, No. 11, Nov. 15, 1962, pp. 766-769.
Riggs, R.D., "Worldwide Distribution of Soybean-Cyst Nematode and Its Economic Importance," Journal of Nematology, vol. 9, No. 1, Jan. 1977, pp. 34-38.
Riggs, R.D., and D.P. Schmitt, "Complete Characterication of the Race Scheme for Heterodera glycines," Journal of Nematology, vol. 20, No. 3, Jul. 1988, pp. 392-395. Rutherfold, R.S., "Prediction of Resistance in Sugarcane to Stalk Borer *Eldana saccharina* By Near-Infrared Spectroscopy on Crude Budscale Extracts: Involvement of Chlorogenates and Flavonoids," Journal of Chemical Ecology, vol. 24, No. 9, 1998, pp. 1447-1463.
Schapaugh, W.T., Jr., P.A. Owen, K.M. Clark, and D.A. Sleper, "Registration of 'Magellan' Soybean," Crop Science, vol. 38, May-Jun. 1998, p. 892.
Schmitt, D.P., and G. Shannon, "Diffrentiating Soybean Responses to Heterodera Glycine Races," Crop Sciende, vol. 32, 1992, pp. 275-277.

(Continued)

*Primary Examiner* — Pablo Whaley
(74) *Attorney, Agent, or Firm* — Lathrop & Gage LLP

(57) ABSTRACT

The present invention relates to a method and apparatus for predicting the resistance of soybean seed samples to infection by soybean cyst nematode parasites using near-infrared spectroscopy and discriminant analysis.

2 Claims, 12 Drawing Sheets

OTHER PUBLICATIONS

Winstead, N.N., C.B. Skotland, and J.N. Sasser, "Soybean Cyst Nematode in North Carolina," Plant Disease Reporter, vol. 39, No. 1, Jan. 15, 1955, pp. 9-11.

Brim, Charles A. and J.P. Ross, "Registration of Pickett Soybeans" (Reg. No. 52), Registration of Varieties, 1966, p. 305.

Epps, James M. and Albert Y. Chambers, "The Soybean Cyst Nematode, Symptoms, Life Cycle, Spread, Host Range, Research on Control", Tenn. Farm Home Sci. Prog. Rep 1962, 1-4.

Hymowitz, T., "On the Domestication of the Soybean," Economic Botany, 1970, pp. 408-417.

Osborne, B.G. and T. Fearn, "Near Infrared Spectroscopy in Food Analysis," Longman Scientific & Technical, John Wiley & Sons, Inc., New York, Nov. 1986, pp. 1-7.

Yue, Pin, "Genetics of Resistance to Heterodera glycines Races in Two Soybean Plant Introductions", May 2000, pp. 1, iv-v.

PCT/US02/05319 International Search Report; Oct. 2002.

PCT/US02/05319 International Preliminary Examination Report; Nov. 13, 2003.

Pazdernik, D.L., et al., Effect of Temperature and Genotype on the Crude Glycinin Fraction (11S) of Soybean and Its Analysis by Near-Infrared Reflectance Spectroscopy (Near-IRS); Apr. 1996, Abstract Only.

* cited by examiner

METHOD AND APPARATUS FOR PREDICTING SOYBEAN SEED RESISTANCE BASED ON NEAR-INFRARED SPECTROSCOPY

CROSS REFERENCE TO RELATED APPLICATIONS

This application claims the benefit of U.S. Provisional Application Ser. No. 60/269,474, filed Feb. 16, 2001, the disclosure of which is herein incorporated by reference.

FIELD OF THE INVENTION

The present invention relates to methods and apparatuses for comparing genotypes of biological tissue samples. Specifically, infrared spectroscopy is used for comparing genotypes of soybean tissue samples, and more particularly for determining resistance to soybean cyst nematode.

BACKGROUND OF THE INVENTION

Chemical bonds in organic molecules absorb energy in the near infrared region of the spectrum. Near infrared reflectance spectroscopy involves measuring the amount of light reflected by the substance to determine the amount of light being absorbed by the substance. Different types of carbon bonds absorb energy at different wavelengths. Determining the amount of light absorbed at a certain wavelength provides insight into which functional groups are in the substance and a quantitative measure of compounds containing these functional groups can be determined.

Near infrared spectroscopy is also employed in chemical imaging, and uses a tunable light source external to the experimental subject to determine its chemical composition. Typically, measurements can be made quickly on all types of samples.

Infrared thermometers have been used in agriculture for measuring temperatures and determining the need for the irrigation of crops. See, for example, U.S. Pat. Nos. 4,301,682 and 4,998,826.

Soybean (*Glycine max* (L.) Merr) is an important agricultural crop grown worldwide. Soybean comprises 52 percent of world oilseed production with 155.1 million metric tons, 46 percent of which were produced in the United States. In 1999, the United States produced 71.9 million metric tons on 29.9 million hectares. The importance of soybean continues to grow as new uses for soybean products are constantly being developed. Soybean has also long been a staple food in many diets. Uses of soybean range from industrial uses such as inks and lubricants to foods and food additives.

As the number of hectares of soybeans grown increases, so does the pressure exerted on soybean by the pathogen, Soybean Cyst Nematode (SCN) (*Heterodera glycines* Inchinohe). Currently, soybean growers practice crop rotation utilizing non-host species to reduce reproduction and populations of SCN. Genetic resistance to SCN has also been identified in soybean and implemented in soybean breeding programs for the development of SCN resistant soybean cultivars. While crop rotation is an effective measure in combating SCN, the use of SCN resistant soybean cultivars allows growers to increase soybean acreage without sacrificing yield to the SCN pathogen.

Breeding soybean for resistance to SCN involves the use of genetically resistant cultivars whose source of resistance is derived from plant introductions (PIs). Many of these PIs exhibit poor phenotypes. Crosses of these PI lines with agronomically desirable, but SCN susceptible phenotypes, result in populations of mixed resistant and susceptible genotypes.

Soybean cyst nematode was first characterized in Asia, but not discovered in the United States until 1954 (Winstead et al. 1955). Since its discovery in North Carolina, SCN has spread throughout all soybean-producing regions in the United States. Yield losses due to SCN in the United States were estimated at 7.6 million metric tons in 1998 (Wrather et al., 2000). This represented an increase of 1.6 million metric tons over 1998 estimates. Soybean cyst nematode is the most damaging pest of soybean today. It is a soil borne pest, which makes it able to spread with the movement of contaminated soil to uncontaminated soil via soil erosion or farm implements (Riggs, 1977).

Soybean cyst nematodes are prolific reproducers with each female being able to produce between 200 and 500 eggs. A cyst is formed by the SCN female to protect the eggs from the environment (Endo, 1964). Once the cyst is broken the eggs are released and they immediately begin to hatch if environmental conditions are conducive to nematode survival. The cysts are easily recognizable on the roots of host plants. Hosts of SCN include soybean, annual lespedeza (*Kummerowia striate* (Thunb.) H. & A.), common vetch (*Vicia saliva* L.), adzuki bean (*Vigna angularis* (Willd.) Ohwi & Ohashi), white lupine (*Lupinus albus* L.), and cowpeas (*Vigna savi*) (Epps and Chambers, 1962).

Plants are continually attacked by a diverse range of phytopathogenic organisms. These organisms cause substantial losses to all crops each year. Traditional approaches for control of plant diseases have been the use of chemical treatment and the construction of interspecific hybrids between resistant crops and their wild-type relatives as sources of resistant germplasm. However, environmental and economic concerns make chemical pesticides undesirable, while the traditional interspecific breeding is inefficient and often cannot eliminate the undesired traits of the wild species. Thus, the discovery of pest and pathogen-resistant genes provides a new approach to control plant disease.

Nematode infection is prevalent in many crops. Nematicides such as Aldicarb® and its breakdown products are known to be highly toxic to mammals. As a result, government restrictions have been imposed on the use of these chemicals.

Several genes responsible for disease resistance have been identified and isolated from plants. See Staskawicz et al. (1995) Science 268:661-667. Recently, the sugar beet Hs1.sup.pro-1 gene that confers resistance to the beet cyst nematode has been cloned. See Cai et al. (1997) Science 275:832-834; and Moffat (1997) Science 275:757. Transformation of plants or plant tissues with the resistance genes can confer disease resistance to susceptible strains. See, for example, PCT Publication WO 93/19181; and Cai et al. (1997) Science 275:832-834.

Near infrared spectroscopy (NIRS; 1000 to 3000 nm) has been used extensively for measuring moisture, protein, starch, and oil contents of seeds of several crop species (Osborne and Fearn, 1986). Plant breeders have successfully used NIRS to select individuals with superior seed or forage quality. However, selections based on genotypic markers have not been extensively tested. Traditionally, calibration equations are developed by correlating spectral data generated by NIRS, with reference data generated from substance analysis using wet chemistry. Calibration equations developed for the purpose of distinguishing genotypes must be based on reference values, which accurately characterize genotypic differences in the calibration population.

Rutherford (1998) examined the use of NIRS to determine resistance of sugarcane (*Saccharum* spp. hybrids) to stalk borer (*Eldana saccharina* Walker). Budscale extracts were used for NIRS analysis as well as analysis by high performance liquid chromatography (HPLC). Reference values were based on field bioassay measurements and resistance was categorized on a scale of one to nine. Limited success was obtained with the study in distinguishing resistance to stalk borer from susceptibility by using equations developed from modified partial least squares regression. An attempt to develop an equation based on one or few peaks using a forward stepwise multiple linear regression proved unsuccessful suggesting pathogen resistance is biochemically complex. It is also worth noting that in this study, prediction of stalk borer resistance in sugarcane based on NIRS was more accurate than prediction based on HPLC.

A study by Delwiche et al. (1999) also suggested the ability of NIRS to make genotypic distinctions. This study looked at the ability of NIRS to distinguish wheat (*Triticum aestivum* L.) lines containing wheat-rye (*Secale cereale* L.) translocations from lines that did not contain the translocation using ground seed. A discriminate analysis was performed on the spectral data to classify samples as either having the translocation or not having the translocation. Classification accuracy ranged from 78 to 99 percent. However, difficulties arose in correctly classifying near-isogenic lines differing only by the translocation and lines that were heterogeneous for the translocation.

Genetic resistance to SCN within soybean germplasm has emerged as the forerunner to overcoming this pathogen. While soybean breeders have had much success in developing SCN resistant germplasm, current methods for selecting this germplasm are labor and resource intensive. A challenge exists for identifying a method of screening germplasm for SCN resistance that does not significantly tax the resources of the modern soybean breeding program yet remains accurate in selecting desirable lines.

Current methodology for screening soybean (*Glycine max* (L.) Merr) genotypes for resistance to soybean cyst nematode (*Heterodera gylcines* Ichinohe) (SCN) involve the use of a labor and resource intensive bioassay that can provide inconsistent results due to heterogeneous populations of SCN. Thus, the development of near infrared spectroscopy (NIRS) as a monitoring and/or comparing system for screening soybean populations for SCN resistance would provide an improvement in the efficiency of the breeding process by saving time and money over current bioassay methods.

SUMMARY OF THE INVENTION

The present invention relates to methods and apparatuses for comparing genotypes of tissue samples.

The invention further relates to the use of infrared spectroscopy for comparing genotypes of tissue samples.

The invention further relates to the use of infrared spectroscopy for comparing genotypes of plant tissue samples.

The invention additionally relates to the use of infrared spectroscopy for comparing genotypes of soybean plant tissue samples.

The invention still further relates to the use of infrared spectroscopy for determining resistance to soybean cyst nematode.

The invention yet further relates to plant breeding programs, plants and plant derivatives, and seeds selected and/or generated from using these methods and apparatuses.

DETAILED DESCRIPTION OF THE INVENTION

Figure 1:
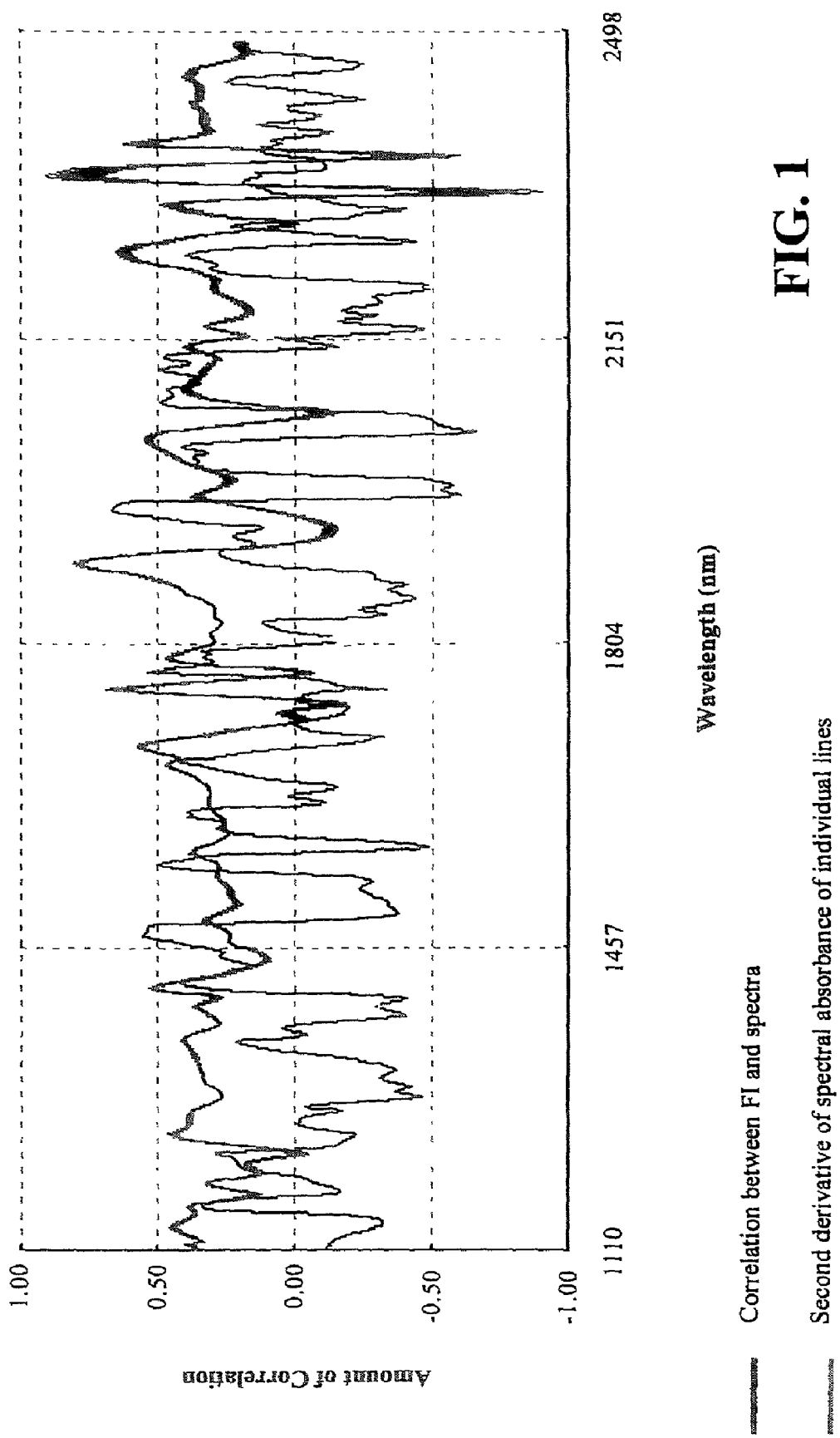
FIG. 1 illustrates the entire spectrum of 77 SCN resistant and susceptible samples with correlation between FI and spectra.

Infrared spectroscopy may be employed in the comparison and analysis of a number of genotypic traits for a variety of tissue samples. Different genotypes in any given genetic locus are reflected in the ultimate chemical composition of a given biological sample. Biological samples may be any suitable type of plant, animal, bacterial, fungal, or viral sample.

Examples of genotypes which may be analyzed in this manner are genotypes which may be comparatively discerned using infrared spectroscopy, which may be general or specific traits, such as, for example, disease resistance, disease susceptibility, enhanced nutritional composition, increased fiber production, increased membrane transport capabilites, increased amino acid content, and the like. Preferred for the practice of the present invention is disease resistance in plants, and preferably the resistance of soybean plants to soybean cyst nematode.

Currently, NIRS is used in agricultural programs to analyze protein and fatty acids. The fundamental principles of NIRS could be used in selection of lines for a number of traits including disease resistance, quality, and physiological traits. This principle can be applied to SCN resistance screening by considering the host-pathogen interaction. Resistant cultivars do not allow reproduction of SCN on their roots. Resistance genes in soybean code for the production of a plant defense response. Several different responses have been detected in soybean. Some of these include the accumulation of peroxidases, polyphenol oxidases, superoxide dismutase, proteinase inhibitors, chitinases, and phytoalexins (Qiu et al., 1997). These responses could be detected through NIRS in resistant cultivars and not in susceptible ones. Roberts et al. (1987) used NIRS to quantify the mold content of hay by analyzing the chitin content in the moldy hay. Nillson et al. (1994) used this same principle to detect anther smut disease (*Microbotryum violacem*) in *Silene dioca*.

NEPS has been successfully used to distinguish between cultivars of sugarcane (Saccharum spp. hybrids) that were resistant and susceptible to Stalk Borer (*Eldana saccharina* Walker) (Rutherford, 1998). Wavelengths corresponding to chlorogenic acid were identified in sugarcane as having different NIR absorptions for resistant and susceptible cultivars. This study used budscale extracts for analysis and regressed spectral data against bioassay data to define equations that could be used to predict sugarcane samples with unknown resistance. Delwiche et al. (1999) used NIRS to identify wheat (*Triticum aestivum* L.) cultivars that contained either the 1AL.1RS or 1BL.1RS wheat-rye (*Secale cereale* L.) translocation using ground wheat seeds. A discriminate analysis using NIRS was used to make the distinction between cultivars with the translocation from cultivars without.

Near infrared spectroscopy is an established method for analyzing plant tissue. However, little data exists on the ability of NIRS to function as a selection tool for genetic pathogen resistance. Near infrared spectroscopy is not a new technology as it has been used extensively in the last half of this century for measuring moisture, protein, starch, and oil contents of seeds of several crop species (Osborne and Fearn, 1986). More recently, NIRS has been useful in measuring the quality of forages (Roberts et al., 1987) and also in quality control in the food processing industry (Bewig, 1992). Importance of NIRS in determining organic constituents is that it is much faster, more repeatable, and easier than traditional methods that involve wet chemistry.

The principle behind NIRS is that many of the chemical bonds in organic molecules will absorb energy in the near infrared region of the light spectrum (Osborne and Fearn, 1986). By measuring the amount of energy transmitted or reflected by the functional group, one can determine the amount of energy absorbed by the substance. This can be correlated to the type of bonds that exist in the substance and the different constituents of the substance and their concentrations can be determined.

While the use of plant tissue samples is feasible in a plant breeding program, the use of mature seeds as a non-destructive analytical means is preferred. The instant invention examined the ability of NIRS to distinguish SCN resistance from susceptibility using ground soybean seed.

Samples are analyzed using NIRS, and the resulting spectra and data are compared to appropriate controls. Calibration equations were developed using different types of reference values for classifying SCN resistance. Spectral data is visually analyzed and peaks are identified. For example, SCN resistant lines showed a different spectral trend than susceptible lines in the resulting spectra.

The data derived from the spectral analysis is then further analyzed using appropriate computer programs, for example.

The following Examples further exemplify the invention.

EXAMPLES

Example 1

Preparation of Plant Materials

Plant Materials:

Two-hundred fifteen experimental soybean cultivars were selected from the University of Missouri's soybean breeding program. These cultivars were selected in the $F_{4:5\&6}$ generations from preliminary yield trials grown in 1999. The cultivars were divided into three groups based on their pedigrees. Seventy-eight experimental cultivars resulted from crosses between two SCN resistant parents and were grouped together. Eighty-two experimental cultivars resulted from crosses between one SCN resistant and one SCN susceptible parent and were grouped together. The final 55 experimental cultivars resulted from crosses between two SCN susceptible parents and were grouped together. Seed quality of these cultivars was generally poor as many seeds were infested with purple seed stain (*Cercospora kikuchii*) as well as phomopsis seed decay (*Phomopsis longicolla* Hobbs). Five hundred seeds were visually selected from each cultivar to ensure that the best quality seed was analyzed.

SCN Bioassay:

The SCN bioassay was performed in the greenhouse using established methods (Rao Arelli et al., 1991 and Arelli et al., 1999). A SCN Race 3 isolate was used for inoculation of the experimental lines. Twenty-five seeds from each line were treated with Captan (N-trichloromethylthio-4-cyclohexene-1,2-dicarboximide) to aid in germination and germinated in germination bags. Five seedlings were transplanted and inoculated with the SCN Race 3 isolate. Race determination was confirmed by reaction to the differential cultivars and to the susceptible cultivar 'Hutcheson' (Buss et al., 1988). The female index (FI) (formerly called index of parasitism, Golden et al. 1970 and Schmitt and Shannon 1992) was used to evaluate the response of each cultivar to the SCN Race 3 isolate. Female index was calculated by dividing the numbers of cysts counted on an experimental line by the number of cysts counted on the SCN susceptible cultivar 'Essex' and multiplying by 100. Cultivars were then classified by their FI as follows: FI=0-9, resistant; FI=10-29, moderately resistant; FI=30-59, moderately susceptible; FI=60+, susceptible.

The bioassay results showed a wide range of infection levels for lines with the same SCN resistance genotype. Because SCN is a genetically dynamic pathogen, gene mapping molecular marker studies would assist in providing genotypic information from breeding lines. The ability to use NIRS to accurately predict SCN reaction in breeding lines rests on the ability to calibrate with static reference values that are characteristic of SCN resistance genotypes.

NIR Spectroscopic Analysis:

Approximately 20 g of seed from each cultivar were ground using a Wiley benchtop grinder to pass through a 1-mm screen during the winter of 2000. Ground seed samples were stored in sealed plastic bags in a freezer at −20° C. Approximately 7 g of ground seed from each cultivar were scanned with a Foss NIRSystems Model 6500 (Foss NIRSystems Silver Spring, Md.). The instrument scanned 7 g from each sample with radiation from 400 to 2498 nm, and log 1/reflectance (log 1/R) was recorded at 2 nm intervals. Spectral data were trimmed to only include NIR portion of the spectrum, which ranges from 1100 to 2498 nm, to eliminate variations between samples due to seed discoloration that appear in the visible region.

Plant Materials:

Nine cultivars were selected for this experiment. These cultivars represented a wide range of genetic diversity for SCN resistance. Differential cultivars for SCN race isolate classification as proposed by Golden et al. (1970) were selected because most SCN resistant commercial soybean cultivars developed their SCN resistance from these cultivars. The differential cultivars 'Peking', 'Pickett' (Brim and Ross, 1966), PI 90763, and PI 88788 along with PI 437654 because of its broad resistance to all known races of SCN. The cultivars 'Essex' and 'Magellan' (Schapaugh et al., 1998) were selected as SCN susceptible checks to determine SCN infection levels. The final two experimentals were two near isogenic lines (NIL) derived from the cultivar 'Bedford'. One of the lines was SCN resistant and designated NIL1 the other was SCN susceptible and designated NIL2.

Calibration equations were developed for the purpose of screening soybean germplasm with unknown reactions to SCN. Calibration equations using NIRS rely on accurate reference data. The SCN bioassay provided reference data for the basis of developing calibration equations for predicting SCN resistance in soybean. Female index was calculated for each experimental line using the susceptible cultivar Essex equal to 100. Essex had an average of 94 females per plant. The SCN. race isolate was confirmed as race 3 by a FI<10 on the differentials, PI 90763, PI 88788, 'Peking', and 'Pickett' (Brim and Ross, 1966). Female index of the experimental cultivars ranged from 0.0 to 163.8. High levels of infection were confirmed by SCN susceptible controls. The SCN susceptible check cultivars had FIs of 78.72, 105.32, 163.83 for the cultivars 'Macon' (Nickell et al. 1996), 'Hamilton' (Nickell, 1989), and 'Hutcheson' (Buss et al. 1988), respectively. Of particular interest were the cultivars Macon and Hamilton as they were used as parents in several of the experimental cultivars containing one or both parents as susceptible to SCN. Some of these experimental lines exhibited transgressive segregation, as their FIs were lower than the FIs of Macon and Hamilton. Yue et al. (2000) suggested the possibility of Hamilton containing minor SCN resistance genes that contributed to its lower R. The data would support the possibility of Macon containing some minor SCN resistance genes as well as Hamilton-Twenty-five lines from crosses with both parents being SCN susceptible received a classification of moderately susceptible based on their FI.

It is also important to note that many of the lines resulting from crosses between one parent that was SCN resistant and one that was SCN susceptible were still segregating for SCN resistance. This suggested that these lines existed as heterogeneous populations containing both SCN resistant and SCN susceptible individuals. This was evident by the wide range of FIs for individual replications in a given line. Female index used for classification of lines was based on the average of all five replications for each line.

Experimental Design:

Three randomized complete blocks were designed, one for each plant tissue harvesting date, 30, 60, and 90 d following SCN inoculation. There were three replications in each block. Each replication consisted of two treatments, one treatment with SCN inoculation and the other treatment without SCN inoculation. This design provided 18 entries per replication and 54 entries per block for each of the three, plant tissue harvesting date for a total of 162 experimental units.

Seeds for each entry were germinated in germination bags for five days. Seedlings for each entry were transplanted into steam sterilized fine sand. For the 30 d harvest treatment, five seedlings were transplanted into each pot. Pots used for the 30 d harvest treatment were 25.5 cm in diameter. Four seedlings per pot were transplanted for each entry in the 60 d harvest treatment while the 90 d treatment only used 3 seedlings per plot. Pot size was increased for both the 60 and 90 d harvest treatments to 35.5 cm diameter to facilitate larger plant growth.

Sixty and 90 d harvest blocks were treated with Miracle-Gro (8-7-6) (The Scotts Company, Marysville, Ohio, USA) 45 d after transplanting to compensate for lack of nitrogen-fixing bacteria in the sterilized soil. Plants were watered daily to maintain optimum plant health. All blocks were bordered with a single row of 25.5 cm diameter pots containing three plants of the cultivar Magellan to minimize border effects.

Inoculation

Soybean cyst nematode inoculum was prepared according to Rao Arelli et al. (1991). Individual plants were inoculated with approximately 5,000 SCN eggs each, two days following seedling transplantation. The SCN race isolate used for inoculation was cultured on the SCN susceptible cultivar 'Hutcheson' (Buss et al., 1988) and was considered race 3. Two applications of 2500 eggs each were placed on opposite sides of individual plants in holes 1 cm in diameter and approximately 5 cm deep using an automatic pipetter (Brewer Automatic Pipetting Machine, Scientific Products, Baltimore, Md., USA).

Harvesting of Plants:

Plants were-harvested on 30 d cycles following inoculation. Plants were harvested by cutting the pots and soaking them in water to allow the soil to slowly dissolve from the roots. Roots were then washed with pressurized water to remove cysts from roots and cysts were collected and counted under a stereomicroscope. It is important to note that roots from entries not receiving inoculation were also washed to insure uniformity among root tissue samples. Following root washing, plant tissue from each entry was separated according to leaf stem, and root tissue. In the 90 d harvest treatment, pod tissue was also harvested from each sample. Plant tissue was collected into cloth bags and frozen at 20° C. and then freeze dried. Once samples were dry, they remained frozen at −20° C. until they were ground.

Example 2

Preparation and Analysis of Tissue Samples

NIR Sample Preparation and Analysis:

Dried plant tissue samples were ground to pass through a 1-mm screen using a cyclone type grinder. Ground samples were then placed into clear, sealable plastic bags and returned to the freezer (−20° C.) to await spectral analysis. Approximately 7 g of ground plant tissue were used for NIR analysis. Tissue samples were analyzed using a Foss NIR Systems Model 6500 (Foss NIR Systems, Silver Spring, Md., USA). The instrument scanned each sample with radiation from 400 to 2498 nm in wavelength and log 1/reflectance (Log 1/R) was recorded at 2 nm intervals. Spectral data were trimmed to include just the near infrared portion of the spectrum, which ranges from 1100 to 2498 nm, to remove variations due to different tissue color.

Data Analysis:

Cysts collected from entries that were inoculated with SCN were counted and female index (FI) (formerly called index of parasitism) was calculated according to Golden et al. (1970) and Schmitt and Shannon (1992). This data was analyzed to confirm established reactions of cultivars, to SCN and to confirm that the race isolate used for inoculation was race 3.

Visualization of Spectra:

Near infrared reflectance spectra were collected and analyzed using WinISI II-Version 1.01 software (Foss NIRSystems, Silver Spring, Md., USA). Reflectance data was plotted every two wavelengths Across the entire spectrum. Math treatment of spectral data consisted of 2,4,4,1 for derivative order, gap, first smoothing, and second smoothing, respectively. The software then allowed a correlation curve to be plotted over the reflectance curves showing correlation between reference values and spectra at every wavelength. Individual peaks in the spectra showing strong correlation to the reference data could then be identified. A protocol for analyzing spectra by averaging the reflectance data of like samples to amplify differences between unlike samples was proposed by Dyer and Feng (1995). Using this protocol, replications within cultivars were averaged and analyzed for visual differences in the spectra.

Reference data used for correlation was derived from bioassay results collected at the time of plant tissue harvest. Female index was calculated from actual cyst counts and used for reference data. Female index is calculated by dividing the number of cysts found on a given cultivar by the number of cysts found on the susceptible cultivar Essex and multiplying by 100.

Figure 2:
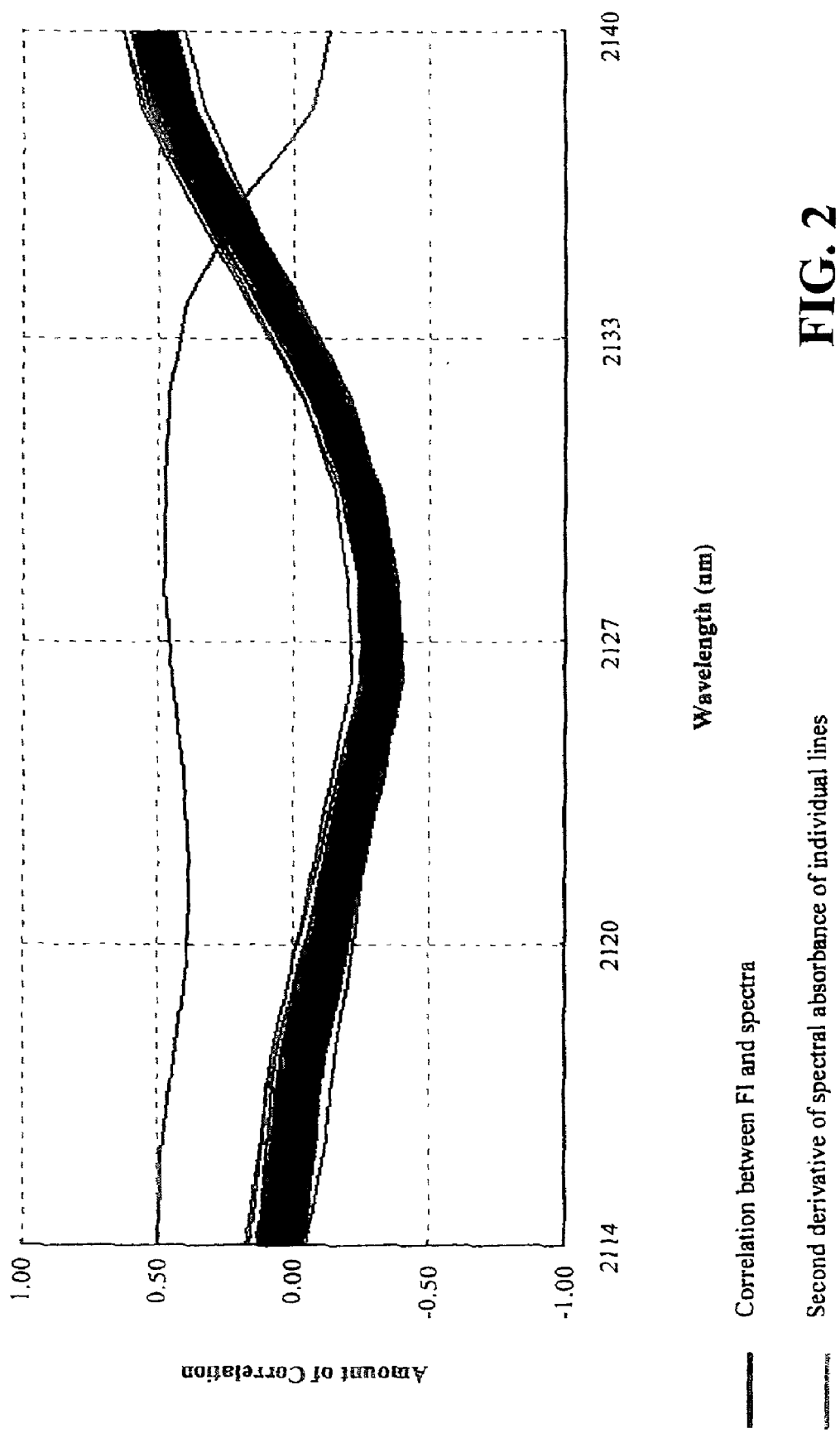
FIG. 2 illustrates a close-up of spectra showing variation for SCN resistance and susceptibility plotted against correlation for FI.
Figure 3:
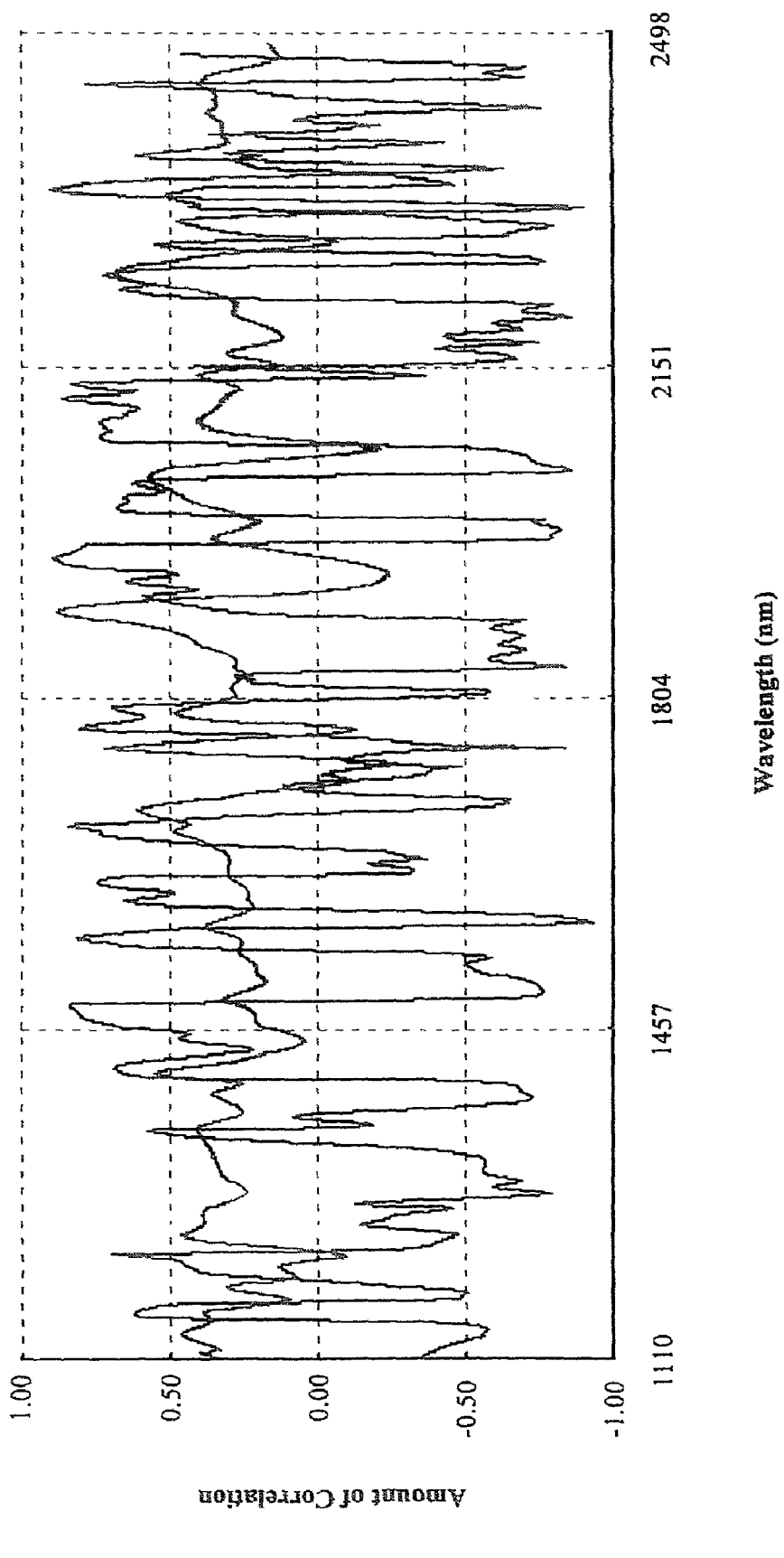
FIG. 3 illustrates the entire spectrum of SCN resistant and susceptible samples averaged by groups of 11 with correlation of FI for each wavelength.
Figure 4:
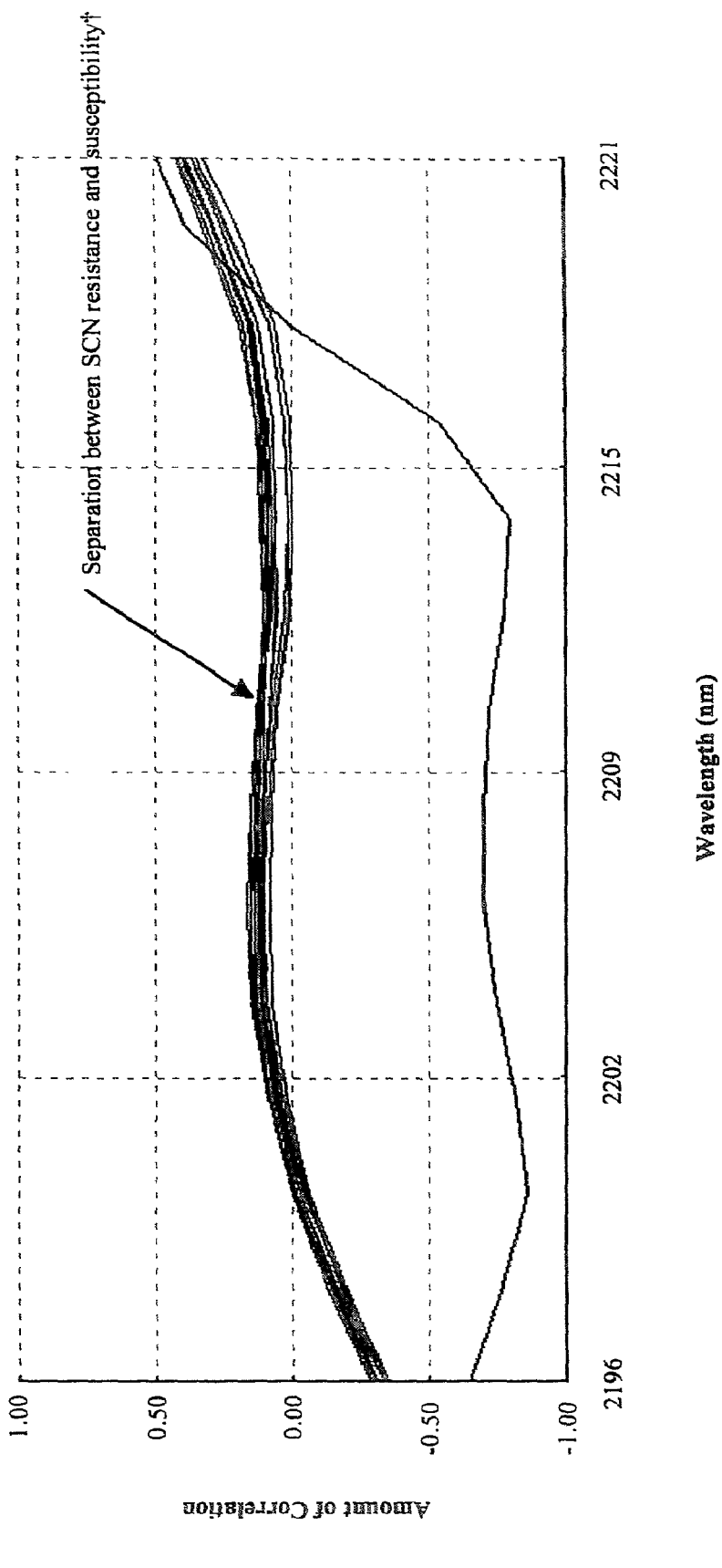
FIG. 4 illustrates a close-up of spectra showing separation between SCN resistance and susceptibility.
Figure 5:
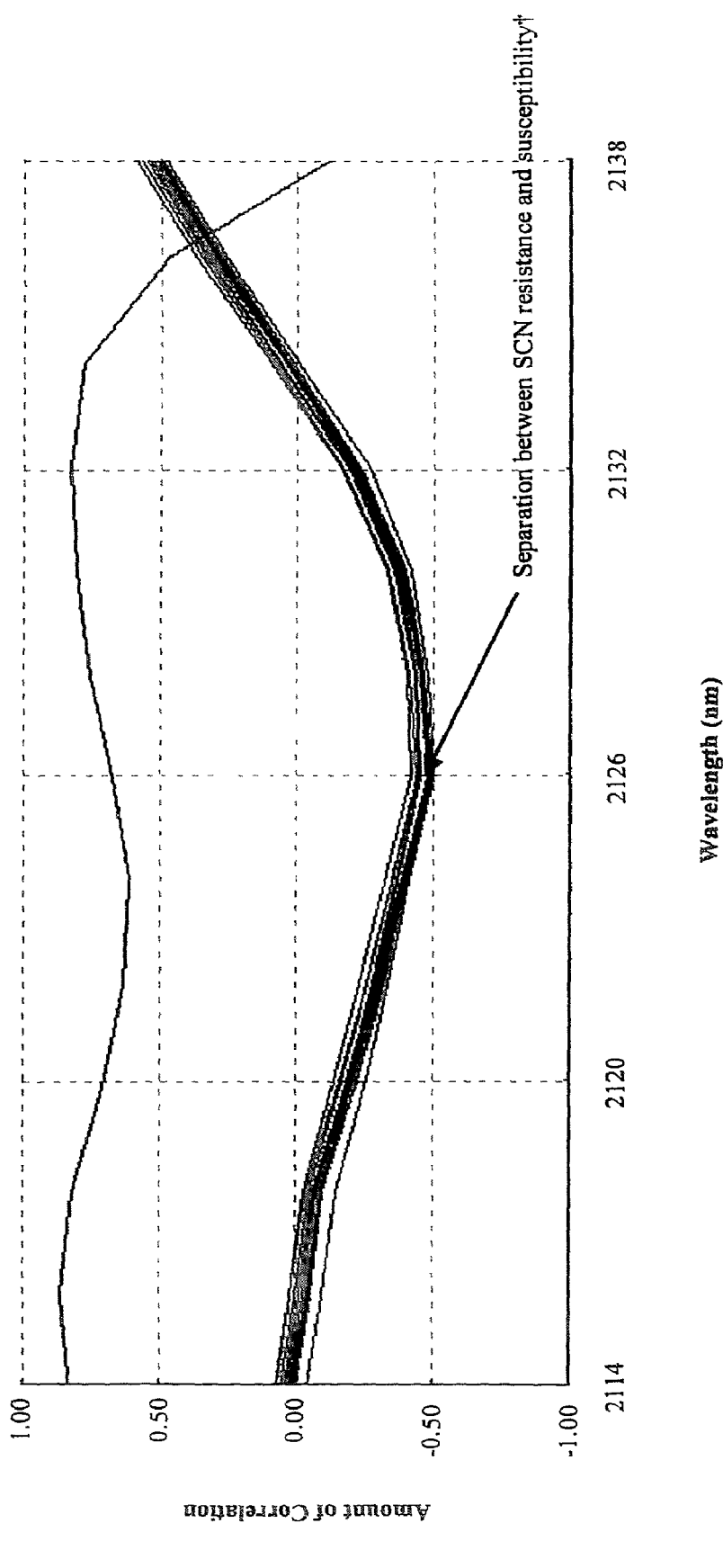
FIG. 5 illustrates another close-up of spectra showing separation between SCN and susceptibility.

Spectral data was analyzed visually to determine if differences between SCN resistant and susceptible lines could be detected by NIRS. FIG. 1 contains the entire population plotted together in red and the correlation of spectral data to FI in black. Several peaks show fairly strong negative or positive correlation to M. FIG. 2 contains a close-up view of the wavelengths surrounding the wavelength at 2127 nm. The black line shows a fairly strong positive correlation between F1 and NIR absorption in this region of the spectrum. The broad red band shows the continuous variation of the population of 132 entries in this region of the spectrum. Studies by Dyer and Feng (1995) and Roberts et al. (1997) suggest developing a population by averaging spectral data of like samples together to maximize differences between groups while maintaining the variation of the original population. FIG. 3 contains the entire spectrum for a population of 12 samples resulting from averaging original population in groups of 11 samples. The resulting population contained 7 SCN resistant entries and 5 susceptible entries. Once again the red line is the entire population plotted together while the black line shows correlation of spectral data to FI. Correlations at individual peaks were much stronger than those in the original population (FIG. 1). However, the peaks were consistent between the two populations. Eight peaks beyond 1900 nm were identified as having strong correlation with SCN resistance. Peaks below 1900 nm are likely associated with water or overtones of the peaks above 1900 nm. Averaging spectral data together amplified differences between SCN resistant and susceptible entries. FIGS. 4 and 5 contain close-ups of regions showing separation between SCN resistant and susceptible entries. Data in FIG. 4 shows distinct separation between SCN resistant and susceptible entries at 221 onm wavelength. Data in FIG. 5 shows distinct separation between SCN resistant and susceptible entries at 2126 nm and again at about 2135 nm wavelength.

Discriminate Analysis:

Because all cultivars used in this experiment are classified as either completely resistant to SCN or completely susceptible, a discriminate analysis was performed to try to distinguish between SCN resistance and susceptibility using NIR data. Cultivars commonly known as SCN resistant were assigned a reference value of one and SCN susceptible cultivars were assigned a value of two. A discriminate analysis was also performed to distinguish between plants that had been inoculated with SCN and those that had not. Entries receiving SCN inoculation were assigned a reference value of one and entries that did not receive SCN inoculation were assigned a value of two. Discriminate analysis used partial least squares regression to discriminate samples on either the basis of inoculation or SCN resistance according to the spectral data from each sample. Each sample was then categorized as correctly falling into its assigned group, incorrectly falling into its assigned group or uncertain as spectral data indicates that the sample could fall into either group. First and second derivatives of log 1/R were used along with the math treatment of 4,4,1 for gap, smooth, and second smooth respectively, however, scatter correction was not used in any discriminate analysis calibrations.

Calibration Equation Development:

Calibration equations for the purpose of predicting SCN resistance were developed. Known reference data collected from bioassay analysis as well as commonly used SCN resistance classifications used in discriminate analysis were regressed against spectral data.

Regression equations were calculated by regressing spectral data against reference values calculated from external data sources such as the SCN bioassay. These equations were developed for purpose of predicting SCN resistance in samples with unknown genotypes. Four different reference values were assigned to each sample based on the SCN bioassay and the pedigree of each sample. The reference values were as follows: Pedigree value 1=samples with both parents SM resistant, 2=samples with one parent SCN resistant and one parent SCN susceptible, 3=samples with both parents SCN susceptible; SCN bioassay 1=resistant; 2=moderately resistant; 3=moderately susceptible, 4=susceptible. Female index and actual cyst counts were also used as reference values.

Equations were developed using a modified partial least squares (MPLS) regression. The first and second derivatives of log 1/R each with and without scatter correction were used in developing calibration equations. Math treatments of the spectral data consisted of 4 for gap, 4 for smooth, and 1 for second smooth. This initial analysis resulted in four separate equations for each source of reference. For each equation, 4 cross validation groups were used and 2 outlier passes were performed. Outliers were selected on the basis of critical 'T'=2.5 and critical 'H'=10.0. Calibration equations were evaluated on the basis of coefficient for determination of calibration ($R^2$), standard error of calibration (SEC), standard error of cross validation (SECV), and validation accuracy (1-VR).

Bioassay:

Female index levels were calculated from entries that were inoculated with SCN at each plant-tissue harvest date. Data in Table 1 shows the average number of cysts per plant and FI for each of the three plant-tissue harvest dates. While data from the 60 d and 90 d harvest dates were consistent with the predictions, the 30 d harvest date produced poor results. Essex, the susceptible control, only produced an average of 4.53 cysts per plant. Essex produced an average of 587.08 and 4055.67 cysts per plant for the 60 d and 90 d harvest dates, respectively. When calculating FI, average number of cysts on Essex was set equal to 100. Average number of cysts were then divided by the average number of cysts on Essex and multiplied by 100. Female index levels on 60 d and 90 d harvest on SCN differential cultivars PI 88798, PI 90763, Peking, and Pickett are all less than 10 indicating that the SCN phenotype used was indeed race 3. Female index numbers on 30 d harvest are inaccurate due to low average number of cysts on Essex. It is also important to note the substantial difference in FI for the two near isogenic lines, NIL 1 and NIL 2. These data confirm that the two lines have different SCN reactions.

Storing of Spectra:

Thirty-day tissue harvest failed to produce enough plant tissue to adequately be analyzed by NIRS. Irregular results from the SCN bioassay were withdrawn from analysis. However, 60 d and 90 d harvests produced ample plant tissue from each root, stem, leaf, and pod for NIRS analysis.

Visualization of Spectra:

Visual analysis allowed the relationship between SCN resistance and spectral data to be identified. The relationship between inoculation treatment and spectral data was also identified. Correlations between SCN resistance and spectral data and correlations between inoculation treatment and spectral data were analyzed for each plant tissue sampled. Results for stem and pod tissue mirrored those for leaf tissue but differences did exist between results gathered for root tissue and the above ground tissues. Only leaf and root tissue will be discussed.

Data in FIG. 1 shows the relationship between reflectance and inoculation treatment. Reflectance data is shown by the thick red curve, which is actually data from all the samples plotted together. Correlation between inoculation treatment and reflectance data is shown by the black curve. The y-axis shows the amount of correlation ranging from −1.0 to 1.0. The correlation curve is fairly constant deviating little from zero, which is no correlation. This suggests little effect of inoculation on reflectance data. Several peaks with correlation of 0.5 or −0.5 can be identified suggesting a relationship can be drawn between SCN resistance and spectral data of soybean leaf tissue (FIG. 2). FIGS. 3 and 4 contain reflectance data from root tissue harvested from the same plants. Data in FIG. 3 shows correlation between inoculation treatment and reflectance data while data in FIG. 4 shows correlation between reflectance and SCN resistance. Again, little correlation exists between inoculation treatment and reflectance data (FIG. 3). Surprisingly, not as many peaks in root tissue strongly correlated with SCN resistance as in leaf tissue (FIG. 4).

Figure 6:
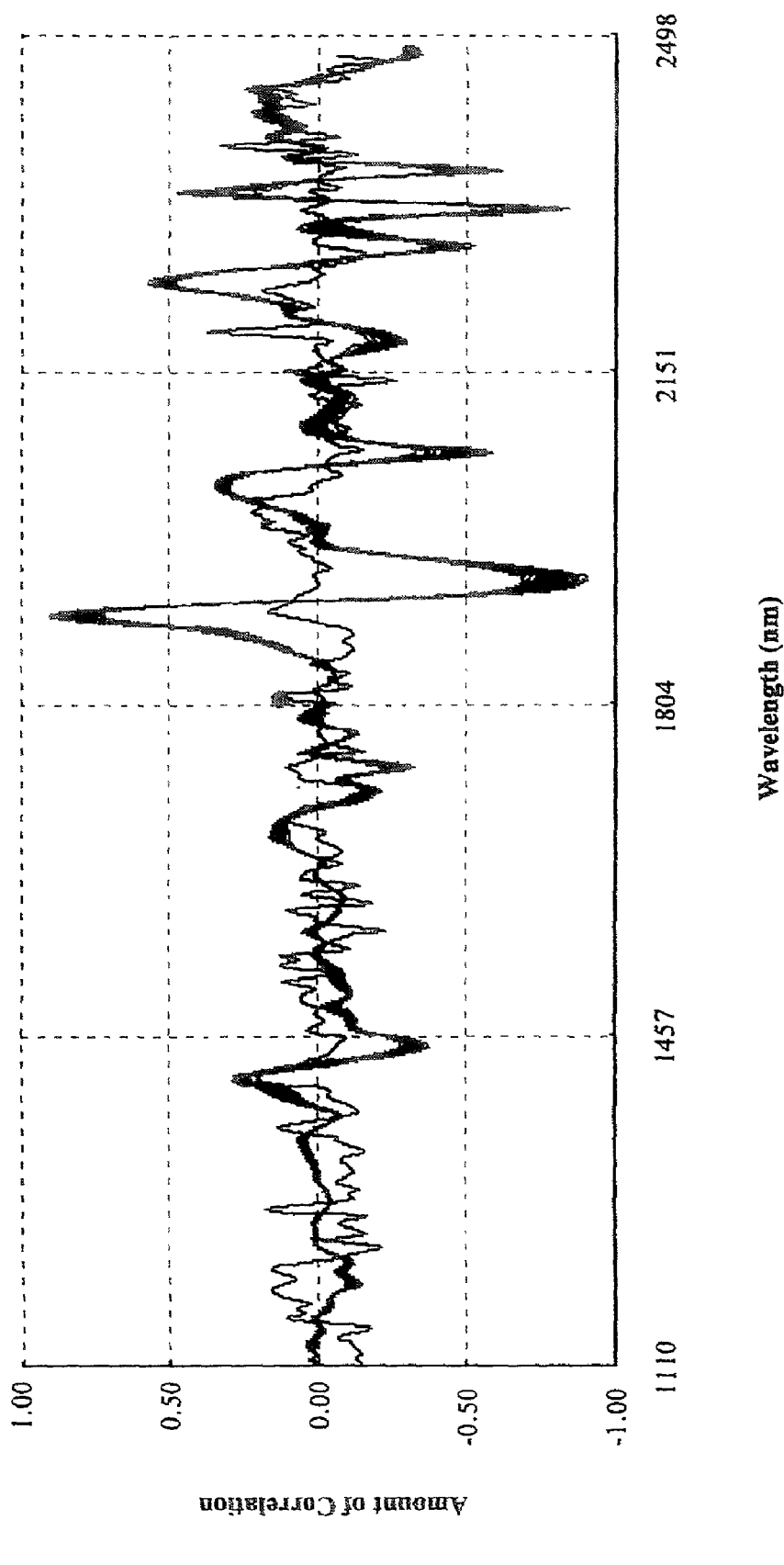
FIG. 6 illustrates the correlation between spectra and inoculation treatment in leaf tissue harvested after 60 days.
Figure 7:
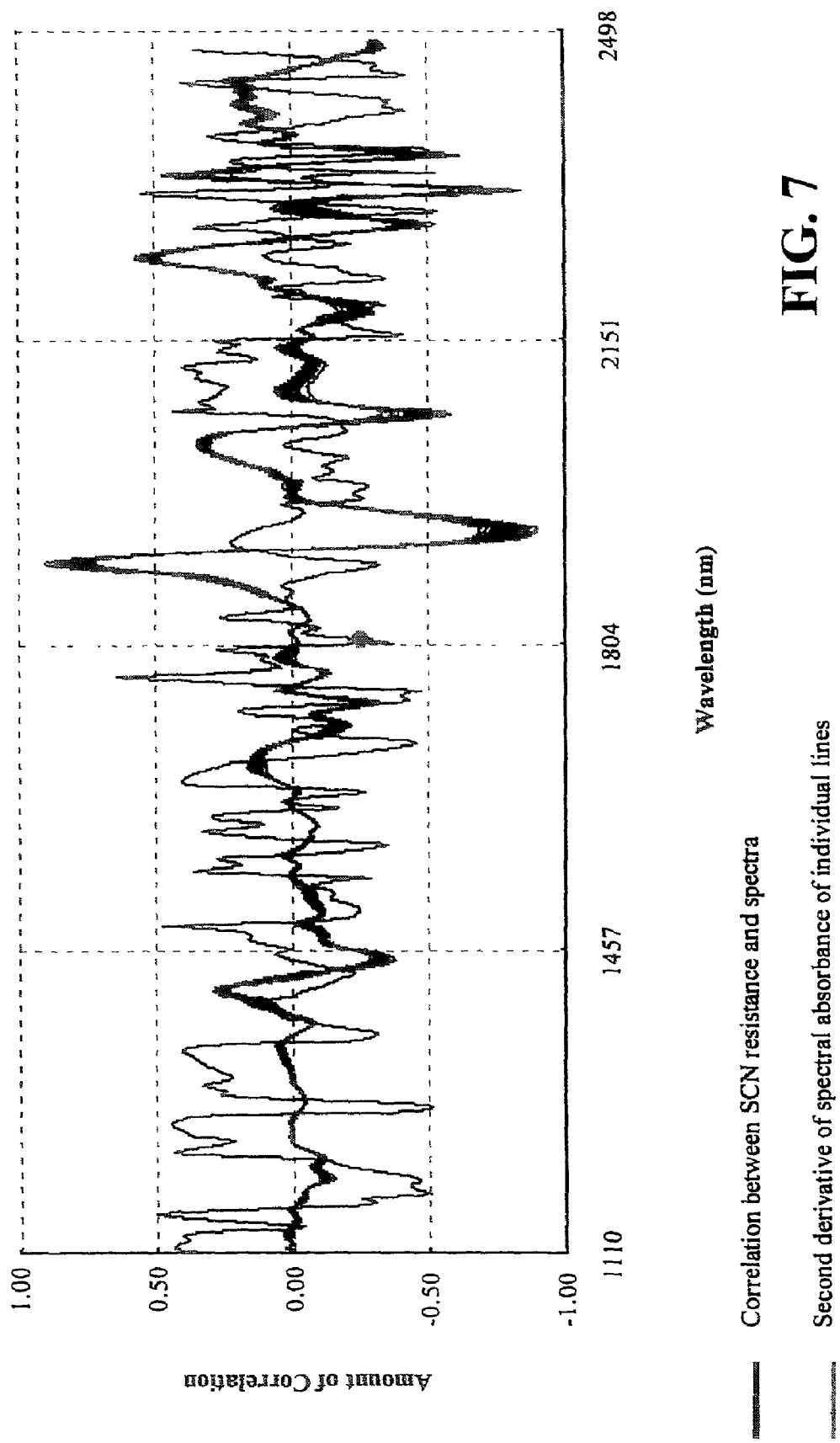
FIG. 7 illustrates the correlation between spectra and SCN resistance in leaf tissue harvested after 60 days.
Figure 8:
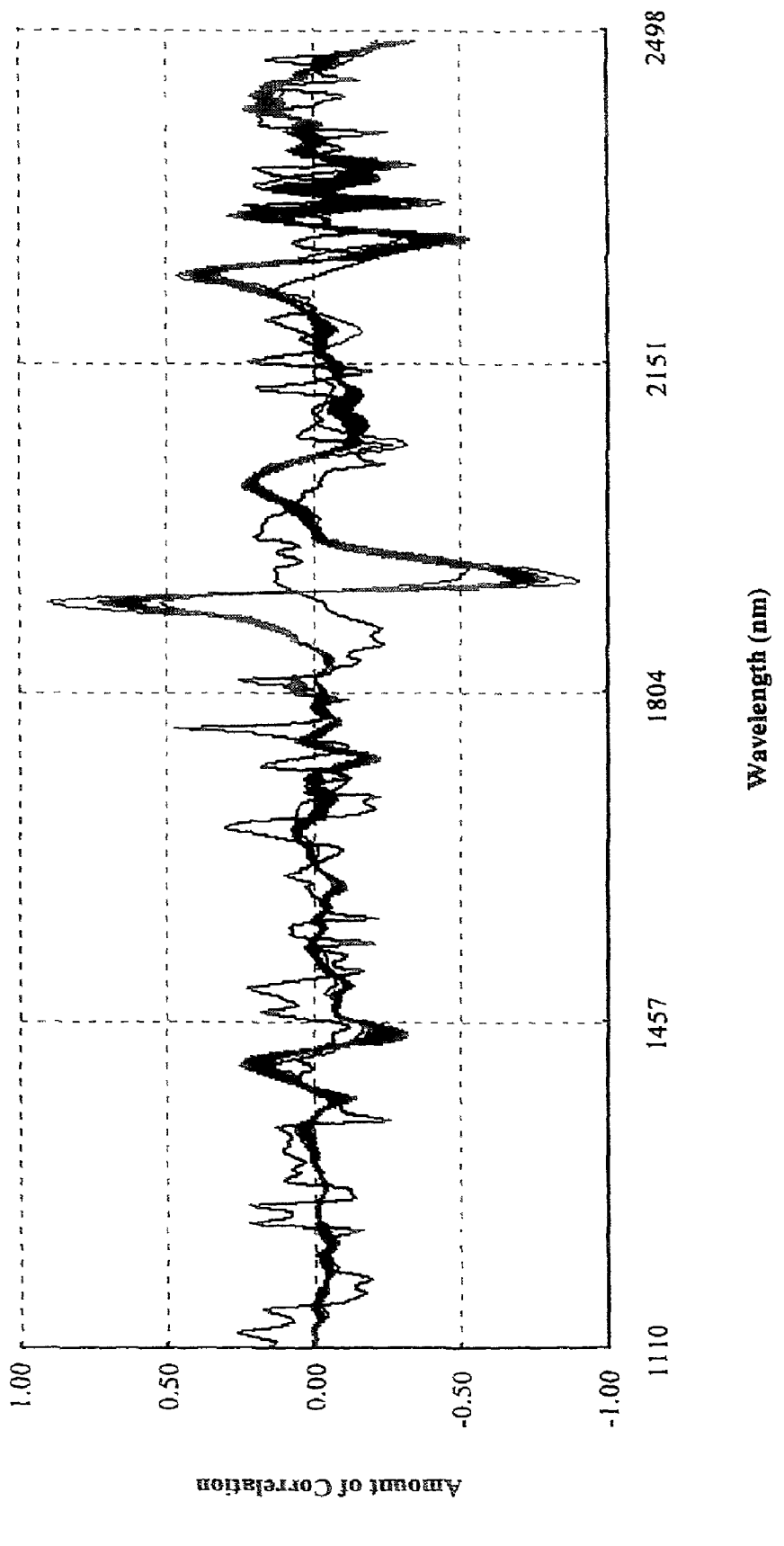
FIG. 8 illustrates the correlation between spectra and inoculation treatment in root tissue harvested after 60 days.
Figure 9:
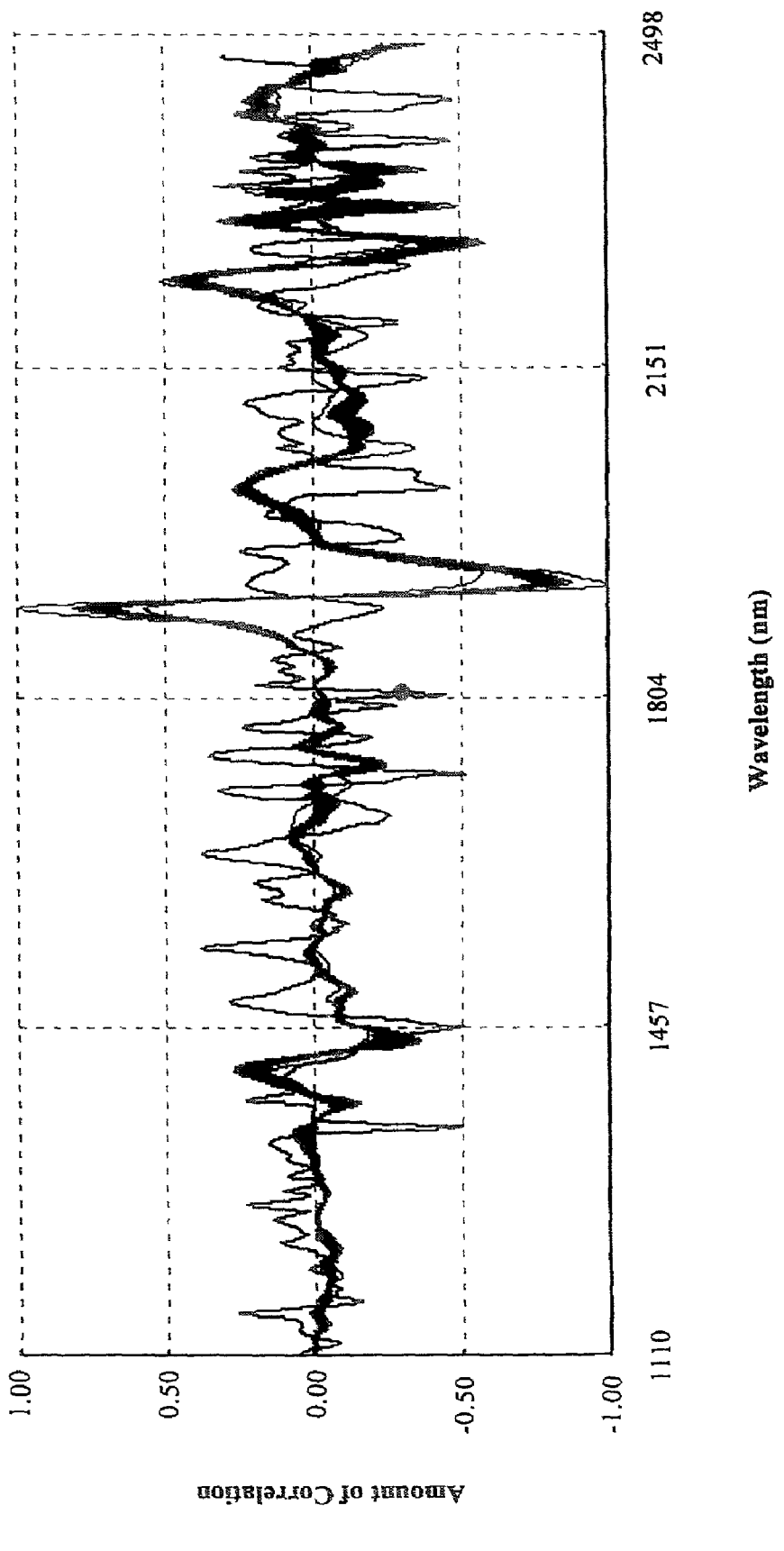
FIG. 9 illustrates the correlation between spectra and SCN resistance in root tissue harvested after 60 days.
Figure 10:
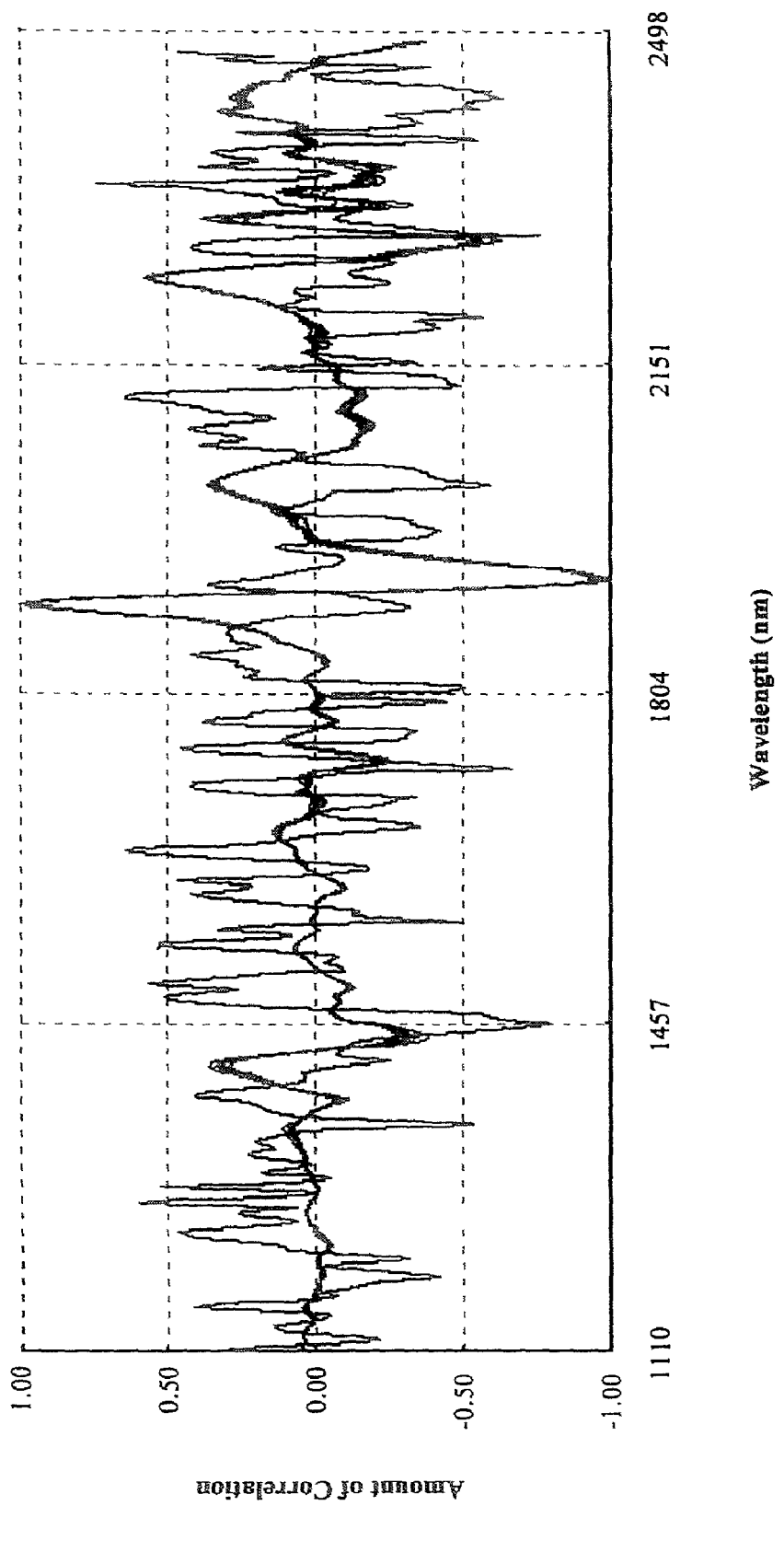
FIG. 10 illustrates the averaged spectra across 3 reps for 60 days root tissue with correlation between FI and spectra.
Figure 11:
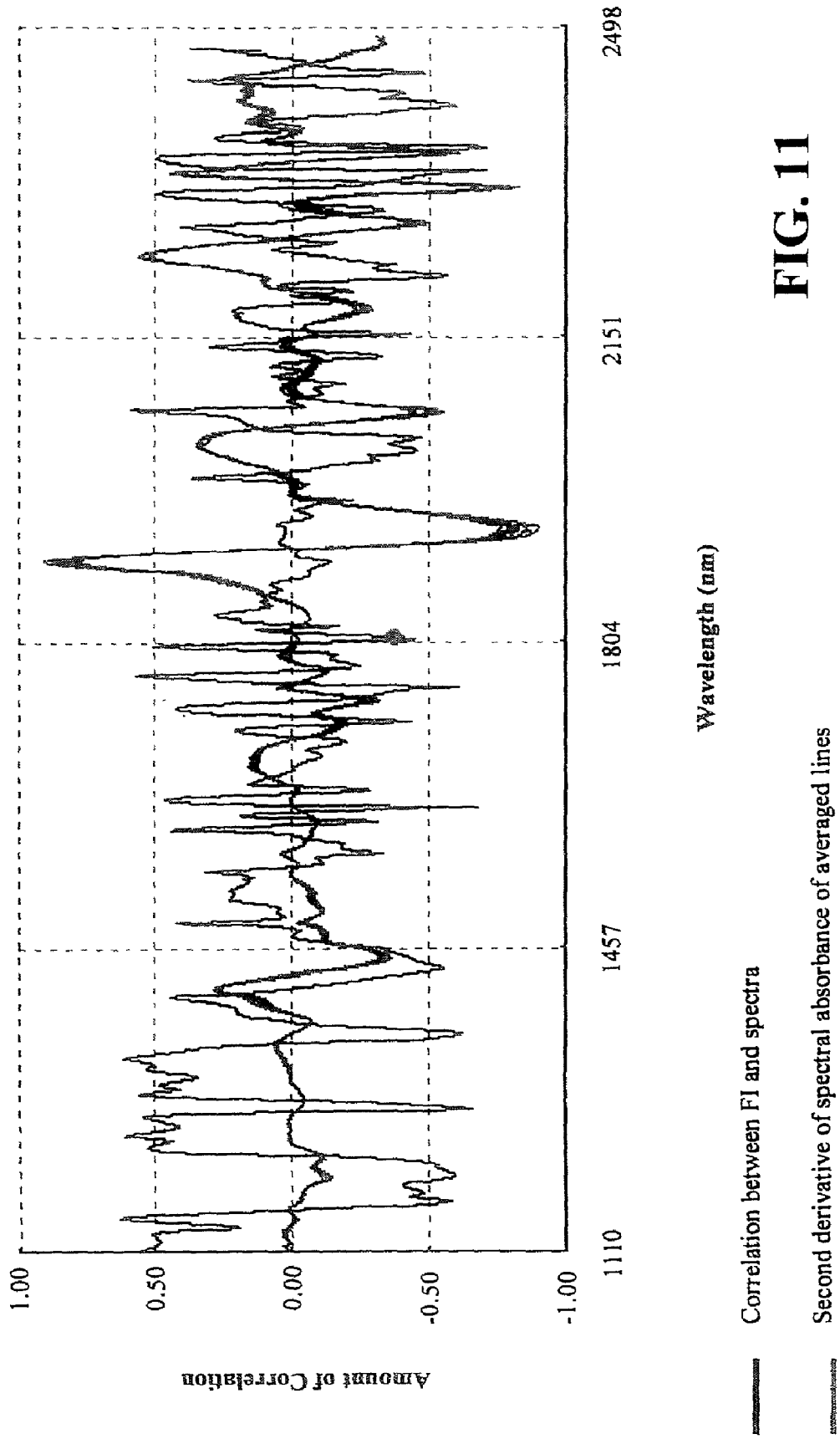
FIG. 11 illustrates the averaged spectra across 3 reps for 60 day leaf tissue with correlation between FI and spectra.
Figure 12:
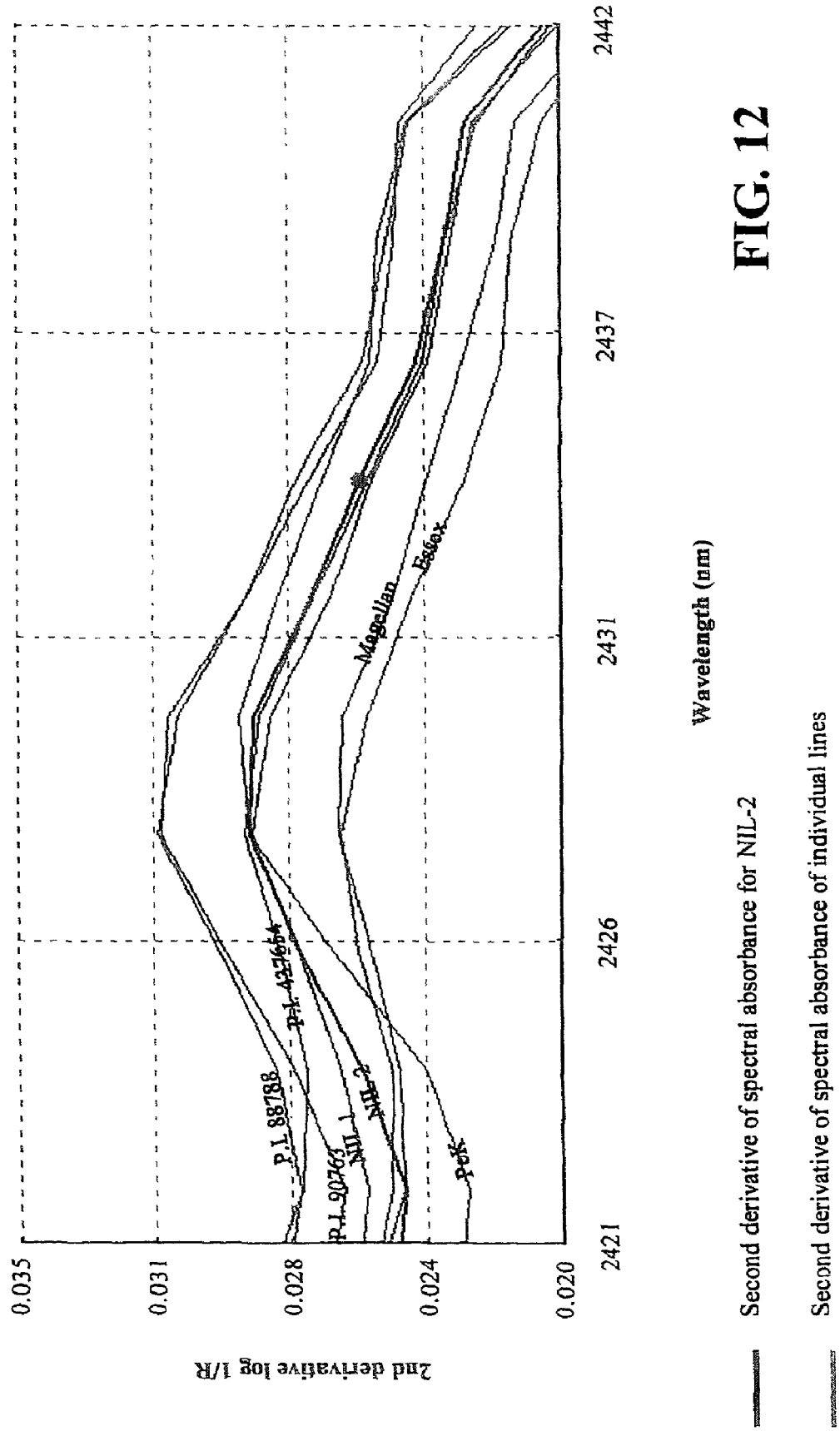
FIG. 12 illustrates the averaged spectra across 3 reps for 60 day root tissue; close-up of separation between SCN resistant and susceptible samples.

Spectra were averaged across replications for each tissue type and plotted against correlation data using FI in an attempt to amplify differences between SCN resistance and susceptibility using actual measurements of resistance. FIGS. 5 and 6 contain correlation of FI with root (FIG. 5) and leaf (FIG. 6) tissue harvested 60 days after SCN inoculation. Both figures show a number of peaks with strong positive and negative correlation to FL. It is important to notice the difference in correlation between data in FIG. 4 and FIG. 5. Data in FIG. 5 shows much stronger correlations between spectra and FI than FIG. 4 showing a simple correlation between SCN resistance classification and spectra.

Discriminate Analysis:

Results from discriminate analysis mirrored results from MPLS analysis. For discriminate analysis, population consisting of averaged spectra from leaf and stem tissue for both 60 and 90-day harvests was used. Using spectral data to discriminate between SCN resistant and susceptible cultivars resulted in no misclassifications and 27 samples uncertain as to which classification they belonged in. The data in Table 2 shows $R^2$ and 1-VR values were relatively high at 0.88 and 0.71, respectively. Discriminate analysis performed with the same population on the basis of whether or not plants were inoculated failed to produce a significant correlation between spectral data and presence of the SCN pathogen.

Calibration Equation Development:

Initially, plant tissue spectral data was separated by tissue type and harvest date. Modified partial least squares regressions performed on these populations showed that no correlation existed between spectral data and whether or not plants were inoculated with SCN. Spectral data from root tissue also failed to produce a correlation between spectral data and SCN reaction-Spectral data from 60 d and 90 d leaf and stem tissue and 90 d pod tissue produce weak correlations between spectral data and SCN reaction (Table 3). It is believed that weak correlations were possibly due to low population size. Given the consistency in SCN reaction as evident by SCN bioassay data, leaf and stem data were averaged together and 60 d and 90 d populations were merged into one. This provided a population size of 82 individual plants. As a result, stronger correlations existed as evident by higher $R^2$ and 1-VR values (Table 4).

Final attempts to increase population size were performed by analyzing individual tissues from leaf, stem, and pod for 60 d and 90 d together. Final population size was 205 samples. While the possibility of calibration equations being over fit exists with the inclusion of more than one individual sample from the same plants, MTLS regressions once again showed a strong correlation between SCN resistance and spectral data, and $R^2$ 1-VR values were high (Table 4).

Data is provided hereinbelow in Tables 1-10, and spectra in FIGS. 1-12.

The results concluded that NIRS could distinguish soybean lines on the basis of SCN resistance using ground soybean seed and ground soybean plant tissue.

Regression analysis of NIR data on the basis of inoculation treatment show that presence of SCN is not required to distinguish between SCN resistant and susceptible genotypes. Visual correlation analysis of spectra also confirm the lack of interaction between inoculation and spectra. This allows breeders to screen populations of experimental lines without having to inoculate them with SCN.

Near infrared spectroscopy provides an alternative to bioassay methods as well as DNA-based markers for selection of SCN resistant genotypes. The data strongly suggests that differences in plant tissue due to SCN resistance exist, and those differences may be found in the NIR spectra. Discrimination between SCN resistant and susceptible soybean lines using infrared spectroscopy was successful.

TABLE 1

Calibration statistics for discriminate analysis performed on two populations of ground soybean seed

| Math Trt.γ | Scatter Correction | N | Detection | Resistant Misclassifications | Susceptible Misclassifications | Uncertain Resistant Classifications | Uncertain Susceptible Classifications | SD£ | SEC¶ | $R^2$ | 1-VR§ |
|---|---|---|---|---|---|---|---|---|---|---|---|
| 2,4,4,1 | none | 128 | 2 | 1 | 2 | 18 | 24 | 0.09 | 0.03 | 0.87 | 0.74 |
| 2,4,4,1 | none | 103 | 2 | 0 | 2 | 13 | 12 | 0.06 | 0.02 | 0..93 | 0.74 |

γMath Treatment - derivative order, gap, $1^{st}$ smooth, $2^{nd}$ smooth

£Standard Deviation

¶Standard Error of Calibration

§1-variance ratio (VR) calculated in cross validation in partial least squares regression

TABLE 2

Calibration statistics for modified partial least squares regression performed on two populations of ground soybean seed

| Constituent | Math Trt.# | Scatter Correction | N | Mean | SD†† | SEC‡‡ | $R^2$ | SEV¶¶ | 1-VR§§ |
|---|---|---|---|---|---|---|---|---|---|
| Pedigree Value† | 1,4,4,1 | None | 209 | 1.8804 | 0.7721 | .0406 | 0.7235 | 0.4756 | 0.6189 |
| Bioassay Class.‡ | 2,4,4,1 | None | 205 | 2.4098 | 1.3053 | 0.5393 | 0.8293 | 0.8364 | 0.5884 |
| Avg # cysts/plant¶ | 2,4,4,1 | None | 207 | 37.7219 | 36.7595 | 19.309 | 0.7217 | 27.9027 | 0.4229 |
| Female Index§ | 2,4,4,1 | SNV & Detrend | 206 | 39.7855 | 38.7855 | 21.799 | 0.6862 | 29.8545 | 0.4107 |
| Pedigree Value | 1,4,4,1 | None | 129 | 1.8062 | 0.9849 | 0.3722 | 0.8572 | 0.4521 | 0.7878 |
| Bioassay Class | 1,4,4,1 | None | 129 | 2.093 | 1.3196 | 0.5419 | 0.8314 | 0.6544 | 0.7523 |
| Avg # cysts/plant | 2,4,4,1 | SNV & Detrend | 122 | 27.1666 | 33.7947 | 14.656 | 0.8119 | 17.7403 | 0.7242 |
| Female Index | 1,4,4,1 | SNV & Detrend | 122 | 27.899 | 34.806 | 14.3007 | 0.8312 | 18.6936 | 0.7101 |

†Pedigree Value: Resistant × Resistant = 1, Resistant × Susceptible = 2, Susceptible × Susceptible = 3
‡Bioassay Classification: FI = 0-9, 1; FI = 10-29, 2; FI = 30-59, 3; FI = 60+, 4
¶Average number of cysts counted per plant from bioassay
§Female Index (FI) = Average number of cysts on experimental line divided by average number of cysts on 'Essex' multiplied by 100
Math Treatment - derivative order, gap, $1^{st}$ smooth, $2^{nd}$ smooth
††Standard Deviation
‡‡Standard Error of Calibration
¶¶Standard Error of Cross Validation
§§1-variance ratio (VR) calculated in cross validation in modified partial least squares regression

TABLE 3

Calibration statistics for modified partial least squares regression performed on population for artificial calibration

| Constituent | Math Trt.† | Scatter Correction | N | # of Outliers | Mean | SD‡ | SEC¶ | $R^2$ | 1-VR§ |
|---|---|---|---|---|---|---|---|---|---|
| % Resistance | 2,4,4,1 | SNV & Detrend | 97 | 4 | 50.79 | 28.39 | 7.41 | 0.93 | 0.62 |

†Math Treatment - derivative order, gap, $1^{st}$ smooth, $2^{nd}$ smooth
‡Standard Deviation
¶Standard Error Calibration
§1-variance ratio (VR) calculated in modified partial least squares regression

TABLE 4

Soybean Cyst Nematode bioassay results from each plant tissue harvest date.

| | 30 Day Harvest | | 60 Day Harvest | | 90 Day Harvest | |
|---|---|---|---|---|---|---|
| | Average Cyst Count† | F.I.‡ | Average Cyst Count | F.I. | Average Cyst Count | F.I. |
| Peking | 0 | 2.9 | 1 | 0.1 | 0 | 0 |
| Pickett | 3 | 64.3 | 34 | 5.8 | 1 | 0 |
| 88788 | 2 | 42.7 | 1 | 0.2 | 45 | 101 |
| 90763 | 1 | 17.1 | 39 | 6.7 | 1 | 0 |
| 437654 | 0 | 3.1 | 13 | 2.2 | 10 | 0.2 |
| ESSEX | 5 | 90.7 | 587 | 100 | 4056 | 100 |
| NIL 1 | 2 | 38.6 | 40 | 6.9 | 4 | 0.1 |
| NIL 2 | 3 | 64 | 395 | 67.3 | 2968 | 73.2 |
| MAGELLAN | 3 | 61.5 | 503 | 85.6 | 1059 | 26.1 |

†Average number of cysts per plant over three replications
‡Female Index

TABLE 5

Calibration statistics from discriminate analysis of soybean plant tissue based on SCN resistance.

| Equation | Math Trt.† | Scatter Correction | N | Detection | Resistant Misclassifications | Susceptible Misclassifications | Uncertain Resistant Classifications | Uncertain Susceptible Classifications | SD‡ | SEC¶ | SECV§ | $R^2$ | 1- |
|---|---|---|---|---|---|---|---|---|---|---|---|---|---|
| SCN Resistance | 2,4,4,1 | None | 83 | 2 | 0 | 0 | 17 | 10 | 0.07 | 0.02 | 0.06 | 0.88 | 0. |

†Math Treatment - derivative order, gap, $1^{st}$ smooth, $2^{nd}$ smooth
‡Standard Deviation
¶Standard Error of Calibration
§Standard Error of Cross Validation
1-Variance Ratio (VR) calculated during partial least squares regression

TABLE 6

Calibration statistics for modified partial least squares regression performed on different plant tissues at different harvests.

| | Constituent | Math Trt.† | Scatter Correction | N | Mean | SD‡ | SEC¶ | SECV§ | $R^2$ | 1-VR# |
|---|---|---|---|---|---|---|---|---|---|---|
| 60d stem tissue | Inoculation Treatment | 2,4,4,1 | SNV & Detrend | 50 | 1.48 | 0.51 | 0.49 | 0.6 | 0.04 | −0.15 |
| | SCN Resistance | 2,4,4,1 | SNV & Detrend | 51 | 1.35 | 0.48 | 0.18 | 0.3 | 0.87 | 0.6 |
| 60d leaf tissue | Inoculation Treatment | 2,4,4,1 | SNV & Detrend | 52 | 1.48 | 0.5 | 0.49 | 0.58 | 0.07 | −0.25 |
| | SCN Resistance | 2,4,4,1 | SNV & Detrend | 52 | 1.35 | 0.48 | 0.23 | 0.35 | 0.78 | 0.46 |
| 90d stem tissue | Inoculation Treatment | 2,4,4,1 | SNV & Detrend | 53 | 1.51 | 0.51 | 0.41 | 0.45 | 0.34 | 0.26 |
| | SCN Resistance | 2,4,4,1 | SNV & Detrend | 53 | 1.33 | 0.48 | 0.21 | 0.31 | 0.81 | 0.56 |
| 90d leaf tissue | Inoculation Treatment | 2,4,4,1 | SNV & Detrend | 54 | 1.52 | 0.5 | 0.4 | 0.51 | 0.3 | 0.07 |
| | SCN Resistance | 2,4,4,1 | SNV & Detrend | 54 | 1.33 | 0.48 | 0.18 | 0.3 | 0.85 | 0.59 |
| 90d pod tissue | Inoculation Treatment | 2,4,4,1 | SNV & Detrend | 52 | 1.5 | 0.51 | 0.5 | 0.58 | −0.001 | −0.17 |
| | SCN Resistance | 2,4,4,1 | SNV & Detrend | 52 | 1.35 | 0.48 | 0.25 | 0.3 | 0.73 | 0.6 |

†Math Treatment - derivative order, gap, $1^{st}$ smooth, $2^{nd}$ smooth
‡Standard Deviation
¶Standard Error of Calibration
§Standard Error of Cross Validation
1-Variance Ration (VR) calculated during partial least squares regression

TABLE 7

Calibration statistics for modified partial least squares regression performed on two soybean plant tissue populations.

| Constituent | Math Trt.† | Scatter Correction | N | Mean | SD‡ | SEC¶ | SECV§ | $R^2$ | 1-VR# |
|---|---|---|---|---|---|---|---|---|---|
| Inoculation Treatment | 2,4,4,1 | none | 80 | 1.5 | 0.5 | 0.48 | 0.5 | 0.08 | 0.01 |
| SCN Resistance | 2,4,4,1 | none | 80 | 1.3 | 0.46 | 0.15 | 0.23 | 0.89 | 0.75 |
| Inoculation Treatment | 2,4,4,1 | none | 203 | 1.5 | 0.5 | 0.5 | 0.52 | 0.02 | −0.08 |
| SCN Resistance | 2,4,4,1 | none | 199 | 1.29 | 0.46 | 0.19 | 0.22 | 0.82 | 0.76 |

†Math Treatment - derivative order, gap, $1^{st}$ smooth, $2^{nd}$ smooth
‡Standard Deviation
¶Standard Error of Calibration
§Standard Error of Cross Validation
1-Variance Ration (VR) calculated during partial least squares regression

TABLE 8

| | REP#1 | | | | REP#2 | | | | REP#3 | | | | Ave over all 3 Reps | Avg FI | |
|---|---|---|---|---|---|---|---|---|---|---|---|---|---|---|---|
| | No. Cysts | No. Plants | AVE. | FI | No. Cysts | No. Plants | AVE. | FI | No. Cysts | No. Plants | AVE. | FI | | | |
| 30 Day Harvest Control = 4.53 | | | | | | | | | | | | | | | |
| Peking | 0 | 5 | 0 | 0.00 | 1 | 4 | 0 | 5.00 | 1 | 5 | 0 | 6.67 | 0 | 2.9 | Peking |
| Pickett | 36 | 4 | 9 | 150.00 | 2 | 5 | 0 | 8.00 | 7 | 5 | 1 | 46.67 | 3 | 64.3 | Pickett |
| 88788 | 16 | 5 | 3 | 53.33 | 16 | 5 | 3 | 64.00 | 0 | 5 | 0 | 0.00 | 2 | 42.7 | 88788 |
| 90762 | 1 | 5 | 0 | 3.33 | 9 | 5 | 2 | 36.00 | 2 | 4 | 1 | 16.67 | 1 | 17.1 | 90763 |
| 437654 | 0 | 4 | 0 | 0.00 | 1 | 4 | 0 | 5.00 | 1 | 5 | 0 | 6.67 | 0 | 3.1 | 437654 |
| ESSEX | 30 | 5 | 6 | 100.00 | 24 | 5 | 5 | 96.00 | 14 | 5 | 3 | 93.33 | 5 | 90.7 | ESSEX |
| NIL 1 | 10 | 5 | 2 | 33.33 | 14 | 5 | 3 | 56.00 | 3 | 4 | 1 | 25.00 | 2 | 38.6 | NIL 1 |
| NIL 2 | 13 | 5 | 3 | 43.33 | 12 | 5 | 2 | 48.00 | 23 | 5 | 5 | 153.33 | 3 | 64.0 | NIL 2 |
| MAGEL-LAN | 20 | 5 | 4 | 66.67 | 12 | 4 | 3 | 60.00 | 8 | 4 | 2 | 66.67 | 3 | 61.5 | MAGEL-LAN |
| | | | | | | | | | | | | | Race XVI | | |
| 60 Day Harvest Control = 587.08 | | | | | | | | | | | | | | | |
| Peking | 2 | 4 | 1 | 0.04 | 1 | 4 | 0 | 0.19 | 3 | 4 | 1 | 0.35 | 1 | 0.1 | Peking |
| Pickett | 411 | 4 | 103 | 7.27 | 0 | 4 | 0 | 0.00 | 0 | 4 | 0 | 0.00 | 34 | 5.8 | Pickett |
| 88788 | 4 | 4 | 1 | 0..7 | 7 | 4 | 2 | 1.32 | 6 | 4 | 2 | 0.70 | 1 | 0.2 | 88788 |
| 90762 | 444 | 4 | 111 | 7.86 | 27 | 4 | 7 | 5.08 | 0 | 4 | 0 | 0.00 | 39 | 6.7 | 90763 |
| 437654 | 3 | 3 | 1 | 0.07 | 113 | 4 | 28 | 21.24 | 0 | 2 | 0 | 0.00 | 13 | 2.2 | 437654 |

TABLE 8-continued

| | REP#1 | | | | REP#2 | | | | REP#3 | | | | Ave over all 3 Reps | Avg FI | |
|---|---|---|---|---|---|---|---|---|---|---|---|---|---|---|---|
| | No. Cysts | No. Plants | AVE. | FI | No. Cysts | No. Plants | AVE. | FI | No. Cysts | No. Plants | AVE. | FI | | | |
| ESSEX | 5653 | 4 | 1413 | 100.02 | 532 | 4 | 133 | 100.00 | 860 | 4 | 215 | 100.00 | 587 | 100.0 | ESSEX |
| NIL 1 | 428 | 4 | 107 | 7.57 | 56 | 4 | 14 | 10.53 | 0 | 4 | 0 | 0.00 | 40 | 6.9 | NIL 1 |
| NIL 2 | 617 | 3 | 206 | 14.56 | 3257 | 8 | 407 | 30.611 | 1654 | 3 | 551 | 256.43 | 395 | 67.3 | NIL 2 |
| MAGELLAN | 2855 | 4 | 714 | 50.51 | 361 | 3 | 120 | 90.48 | 2312 | 4 | 578 | 268.84 | 503 | 85.6 | MAGELLAN |

90 Day Harvest Control = 4055.67

| | | | | | | | | | | | | | | | |
|---|---|---|---|---|---|---|---|---|---|---|---|---|---|---|---|
| Peking | 0 | 3 | 0 | 0.00 | 0 | 3 | 0 | 0.00 | 3 | 3 | 1 | 0.03 | 0 | 0.0 | Peking |
| Pickett | 6 | 3 | 2 | 0.03 | 0 | 3 | 0 | 0.00 | 0 | 3 | 0 | 0.00 | 1 | 0.0 | Pickett |
| 88788 | 3 | 3 | 1 | 0.01 | 20 | 3 | 7 | 0.39 | 382 | 3 | 127 | 3.54 | 45 | 1.1 | 88788 |
| 90762 | 1 | 3 | 0 | 0.00 | 2 | 3 | 1 | 0.04 | 2 | 3 | 1 | 0.02 | 1 | 0.0 | 90763 |
| 437654 | 0 | 3 | 0 | 0.00 | | 0 | | 0.00 | 40 | 1 | 40 | 1.11 | 10 | 0.2 | 437654 |
| ESSEX | 20619 | 3 | 6873 | 100.00 | 5103 | 3 | 1701 | 100.00 | 10779 | 3 | 3593 | 100.00 | 4056 | 100.0 | ESSEX |
| NIL 1 | 21 | 3 | 7 | 0.10 | 5 | 3 | 2 | 0.10 | | | | 0.00 | 4 | 0.1 | NIL 1 |
| NIL 2 | 9475 | 3 | 3158 | 45.95 | 10960 | 3 | 3653 | 214.78 | 6277 | 3 | 2092 | 58.23 | 2968 | 73.2 | NIL 2 |
| MAGELLAN | 1794 | 3 | 598 | 8.70 | 480 | 3 | 160 | 9.41 | 7254 | 3 | 2418 | 67.30 | 1059 | 26.1 | MAGELLAN |

Race III

TABLE 9

| SCN Treatment | SCN Inoculated | | | Non-Inoculated | | |
|---|---|---|---|---|---|---|
| Tissue Harvest | 30 days | 60 days | 90 days | 30 days | 60 days | 90 days |
| NIL 1 | 3 reps | 3 reps | 3 reps | 3 reps | 3 reps | 3 reps |
| NIL 2 | 3 reps | 3 reps | 3 reps | 3 reps | 3 reps | 3 reps |
| Essex | 3 reps | 3 reps | 3 reps | 3 reps | 3 reps | 3 reps |
| P.I. 88788 | 3 reps | 3 reps | 3 reps | 3 reps | 3 reps | 3 reps |
| Peking | 3 reps | 3 reps | 3 reps | 3 reps | 3 reps | 3 reps |
| P.I. 90763 | 3 reps | 3 reps | 3 reps | 3 reps | 3 reps | 3 reps |
| Pickett | 3 reps | 3 reps | 3 reps | 3 reps | 3 reps | 3 reps |
| P.I. 437654 | 3 reps | 3 reps | 3 reps | 3 reps | 3 reps | 3 reps |
| Magellan | 3 reps | 3 reps | 3 reps | 3 reps | 3 reps | 3 reps |
| Totals | 27 | 27 | 27 | 27 | 27 | 27 |
| | | | | 162 Total Plots* | | |

*162 plots harvested for root, stem, and leaf tissue for 30 and 60 day treatments with pod tissue added to 90 day treatments

TABLE 10

| Entry # | Plant 1 | Plant 2 | Plant 3 | Plant 4 | Plant 5 | Plant 6 | Average Number of Cysts per Plant | FI | SCN Resistance Rating | SCN Pedigree |
|---|---|---|---|---|---|---|---|---|---|---|
| 1 | 4 | 7 | 4 | 1 | | | 4.00 | 4.26 | 1 | Res × Res |
| 2 | 0 | 0 | 2 | 5 | 0 | | 1.40 | 1.49 | 1 | Res × Res |
| 3 | 1 | 5 | 1 | 7 | 5 | | 3.80 | 4.04 | 1 | Res × Res |
| 4 | 3 | 2 | 5 | 6 | 1 | | 3.40 | 3.62 | 1 | Res × Res |
| 5 | 0 | 2 | 1 | 0 | 0 | | 0.60 | 0.64 | 1 | Res × Res |
| 6 | 2 | 3 | 2 | 0 | 2 | | 1.80 | 1.91 | 1 | Res × Res |
| 7 | 2 | 0 | 3 | 2 | | | 1.75 | 1.86 | 1 | Res × Res |
| 8 | 1 | 0 | 4 | | | | 1.67 | 1.77 | 1 | Res × Res |
| 9 | 0 | 7 | 5 | 5 | 3 | | 4.00 | 4.26 | 1 | Res × Res |
| 10 | 1 | 0 | 2 | 1 | 1 | | 1.00 | 1.06 | 1 | Res × Res |
| 11 | 7 | 13 | 0 | 9 | 12 | | 8.20 | 8.72 | 1 | Res × Res |
| 12 | 1 | 0 | 6 | 2 | 2 | | 2.20 | 2.34 | 1 | Res × Res |
| 13 | 0 | 0 | 1 | 0 | 0 | | 0.20 | 0.21 | 1 | Res × Res |
| 14 | 1 | 1 | 2 | 6 | 0 | | 2.00 | 2.13 | 1 | Res × Res |
| 15 | 0 | 0 | 1 | | | | 0.33 | 0.35 | 1 | Res × Res |
| 16 | 2 | 0 | 0 | 2 | 1 | | 1.00 | 1.06 | 1 | Res × Res |
| 17 | 1 | 0 | 2 | 2 | | | 1.25 | 1.33 | 1 | Res × Res |
| 18 | 2 | 0 | 8 | 2 | 0 | | 2.40 | 2.55 | 1 | Res × Res |
| 19 | 2 | 4 | 1 | 1 | 0 | | 1.60 | 1.70 | 1 | Res × Res |
| 20 | 2 | 0 | 2 | 1 | | | 1.25 | 1.33 | 1 | Res × Res |
| 21 | 1 | 2 | 0 | 0 | | | 0.75 | 0.80 | 1 | Res × Res |
| 22 | 2 | 2 | 1 | 4 | | | 2.25 | 2.39 | 1 | Res × Res |
| 23 | 2 | 7 | 6 | | | | 5.00 | 5.32 | 1 | Res × Res |
| 24 | 0 | 5 | 1 | | | | 2.00 | 2.13 | 1 | Res × Res |

TABLE 10-continued

| Entry # | Plant 1 | Plant 2 | Plant 3 | Plant 4 | Plant 5 | Plant 6 | Average Number of Cysts per Plant | FI | SCN Resistance Rating | SCN Pedigree |
|---|---|---|---|---|---|---|---|---|---|---|
| 25 | 3 | 3 | 2 | | | | 2.67 | 2.84 | 1 | Res × Res |
| 26 | 1 | 2 | 1 | 1 | 3 | | 1.60 | 1.70 | 1 | Res × Res |
| 27 | 3 | 0 | 0 | 3 | | | 1.50 | 1.60 | 1 | Res × Res |
| 28 | 5 | 2 | 1 | 2 | | | 2.50 | 2.66 | 1 | Res × Res |
| 29 | 3 | 0 | 2 | 2 | 3 | | 2.00 | 2.13 | 1 | Res × Res |
| 30 | 1 | 0 | 0 | 2 | 1 | | 0.80 | 0.85 | 1 | Res × Res |
| 31 | 3 | 11 | 0 | 4 | | | 4.50 | 4.79 | 1 | Res × Res |
| 32 | 0 | 3 | 0 | | | | 1.00 | 1.06 | 1 | Res × Res |
| 33 | 0 | 0 | 1 | 0 | | | 0.25 | 0.27 | 1 | Res × Res |
| 34 | 2 | 10 | 0 | 3 | 2 | | 3.40 | 3.62 | 1 | Res × Res |
| 35 | 1 | 2 | 2 | 4 | 0 | | 1.80 | 1.91 | 1 | Res × Res |
| 36 | 1 | 1 | 2 | 1 | | | 1.25 | 1.33 | 1 | Res × Res |
| 37 | 0 | 2 | 2 | | | | 1.33 | 1.42 | 1 | Res × Res |
| 38 | 7 | 2 | 1 | 1 | | | 2.75 | 2.93 | 1 | Res × Res |
| 39 | 0 | 5 | 9 | 6 | 9 | | 5.80 | 6.17 | 1 | Res × Res |
| 40 | 13 | 4 | 5 | 1 | 3 | | 5.20 | 5.53 | 1 | Res × Res |
| 41 | 1 | 0 | 1 | 1 | 2 | | 1.00 | 1.06 | 1 | Res × Res |
| 42 | 3 | 2 | 4 | 0 | 0 | | 1.80 | 1.91 | 1 | Res × Res |
| 43 | 0 | 2 | 3 | 0 | | | 1.25 | 1.33 | 1 | Res × Res |
| 44 | 7 | 3 | 2 | 1 | | | 3.25 | 3.46 | 1 | Res × Res |
| 45 | 1 | 5 | 2 | 2 | 5 | | 3.00 | 3.19 | 1 | Res × Res |
| 46 | 8 | 0 | 10 | | | | 6.00 | 6.38 | 1 | Res × Res |
| 47 | 1 | 3 | 5 | 3 | | | 3.00 | 3.19 | 1 | Res × Res |
| 48 | 4 | 4 | 1 | 6 | | | 3.75 | 3.99 | 1 | Res × Res |
| 49 | 4 | 2 | 25 | 0 | 2 | | 6.60 | 7.02 | 1 | Res × Res |
| 50 | 1 | 4 | 4 | 0 | 3 | | 2.40 | 2.55 | 1 | Res × Res |
| 51 | 1 | 1 | 5 | | | | 2.33 | 2.48 | 1 | Res × Res |
| 52 | 8 | 6 | 2 | 12 | 3 | | 6.20 | 6.60 | 1 | Res × Res |
| 53 | 19 | 6 | 10 | 4 | 7 | | 9.20 | 9.79 | 1 | Res × Res |
| 54 | 7 | 5 | 11 | 4 | 1 | | 5.60 | 5.96 | 1 | Res × Res |
| 55 | 16 | 10 | 3 | 10 | 2 | | 8.20 | 8.72 | 1 | Res × Res |
| 56 | 3 | 6 | 2 | 6 | 0 | | 3.40 | 3.62 | 1 | Res × Res |
| 57 | 2 | | 0 | 5 | 6 | | 2.80 | 2.98 | 1 | Res × Res |
| 58 | 2 | 1 | 2 | | | | 1.33 | 1.42 | 1 | Res × Res |
| 59 | 0 | 0 | 1 | 18 | 5 | | 5.60 | 5.96 | 1 | Res × Res |
| 60 | 11 | 4 | 1 | 6 | 2 | 8 | 5.17 | 5.50 | 1 | Res × Res |
| 61 | 3 | 3 | 15 | 7 | 7 | | 8.20 | 8.72 | 1 | Res × Res |
| 62 | 3 | 9 | 6 | | | | 5.00 | 5.32 | 1 | Res × Res |
| 63 | 10 | 6 | 3 | 9 | 11 | | 7.00 | 7.45 | 1 | Res × Res |
| 64 | 1 | 2 | 3 | 2 | 2 | | 2.00 | 2.13 | 1 | Res × Res |
| 65 | 8 | 2 | 6 | 0 | 3 | | 3.40 | 3.62 | 1 | Res × Res |
| 66 | 1 | 0 | 1 | | | | 4.00 | 4.26 | 1 | Res × Res |
| 67 | 1 | 10 | 1 | | | | 0.67 | 0.71 | 1 | Res × Res |
| 68 | 3 | 0 | 0 | 2 | 23 | | 5.60 | 5.96 | 1 | Res × Res |
| 69 | 7 | 0 | 13 | 11 | | | 9.25 | 9.84 | 1 | Res × Res |
| 70 | 5 | 6 | 11 | 3 | | | 7.00 | 7.45 | 1 | Res × Res |
| 71 | 3 | 9 | 1 | 9 | 2 | | 4.00 | 4.26 | 1 | Res × Res |
| 72 | 2 | 5 | 14 | 1 | 1 | | 5.60 | 5.96 | 1 | Res × Res |
| 73 | 6 | 10 | 3 | 11 | 1 | | 8.20 | 8.72 | 1 | Res × Res |
| 74 | 6 | 20 | 1 | | | | 4.33 | 4.61 | 1 | Res × Res |
| 75 | 8 | 6 | 4 | 13 | 5 | 7 | 6.33 | 6.74 | 1 | Res × Res |
| 76 | 0 | 1 | 0 | 0 | 1 | | 0.20 | 0.21 | 1 | Res × Res |
| 77 | 1 | 0 | 3 | 0 | | | 1.50 | 1.60 | 1 | Res × Res |
| 78 | 7 | 2 | 6 | 2 | 3 | | 4.80 | 5.11 | 1 | Res × Susc |
| 79 | 12 | 6 | 3 | 4 | 48 | | 15.60 | 16.60 | 2 | Res × Susc |
| 80 | 3 | 11 | 80 | 82 | 46 | | 46.60 | 49.57 | 3 | Res × Susc |
| 81 | 2 | 22 | 91 | 4 | 9 | | 43.00 | 45.74 | 3 | Res × Susc |
| 82 | 0 | 109 | 55 | 5 | 73 | | 39.20 | 41.70 | 3 | Res × Susc |
| 83 | 65 | 63 | 69 | 48 | 19 | | 42.00 | 44.68 | 3 | Res × Susc |
| 84 | 118 | 9 | 5 | 40 | 94 | | 63.40 | 67.45 | 4 | Res × Susc |
| 85 | 90 | 60 | 106 | 70 | 61 | | 82.80 | 88.09 | 4 | Res × Susc |
| 86 | 15 | 87 | 4 | 38 | 7 | | 14.20 | 15.11 | 2 | Res × Susc |
| 87 | 4 | 7 | 4 | 5 | 4 | | 4.00 | 4.26 | 1 | Res × Susc |
| 88 | 3 | 3 | 27 | 12 | 47 | | 34.40 | 36.60 | 3 | Res × Susc |
| 89 | 3 | 83 | 9 | 8 | 6 | | 5.80 | 6.17 | 1 | Res × Susc |
| 90 | 114 | 3 | 35 | 74 | 56 | | 65.60 | 69.79 | 4 | Res × Susc |
| 91 | 81 | 49 | 8 | 0 | | | 38.50 | 40.96 | 3 | Res × Susc |
| 92 | 15 | 65 | 16 | 25 | 21 | | 23.80 | 25.32 | 2 | Res × Susc |
| 93 | 42 | 42 | 62 | 89 | | | 49.25 | 52.39 | 3 | Res × Susc |
| 94 | 93 | 4 | 52 | 62 | 95 | | 73.00 | 77.66 | 4 | Res × Susc |
| 95 | 109 | 63 | 73 | 86 | 66 | | 74.80 | 79.57 | 4 | Res × Susc |
| 96 | 1 | 40 | 12 | 109 | 29 | | 40.80 | 43.40 | 3 | Res × Susc |
| 97 | 43 | 53 | 13 | 29 | 12 | | 20.20 | 21.49 | 2 | Res × Susc |
| 98 | 12 | 4 | 11 | 12 | 6 | | 10.80 | 11.49 | 2 | Res × Susc |
| 99 | 1 | 13 | 3 | | | | 2.33 | 2.48 | 1 | Res × Susc |

TABLE 10-continued

| Entry # | Plant 1 | Plant 2 | Plant 3 | Plant 4 | Plant 5 | Plant 6 | Average Number of Cysts per Plant | FI | SCN Resistance Rating | SCN Pedigree |
|---|---|---|---|---|---|---|---|---|---|---|
| 100 | 89 | 3 | 59 | 95 | 81 | | 79.40 | 84.47 | 4 | Res × Susc |
| 101 | 2 | 73 | 8 | 18 | 3 | | 6.60 | 7.02 | 1 | Res × Susc |
| 102 | 7 | 2 | 3 | 1 | 5 | | 3.40 | 3.62 | 1 | Res × Susc |
| 103 | 75 | 1 | 78 | | | | 68.67 | 73.05 | 4 | Res × Susc |
| 104 | 5 | 53 | 2 | 6 | | | 3.50 | 3.72 | 1 | Res × Susc |
| 105 | 2 | 1 | 0 | 6 | 3 | | 2.60 | 2.77 | 1 | Res × Susc |
| 106 | 76 | 2 | 30 | 51 | 56 | | 54.20 | 57.66 | 3 | Res × Susc |
| 107 | 10 | 58 | 0 | 3 | 12 | | 6.20 | 6.60 | 1 | Res × Susc |
| 108 | 8 | 6 | 1 | 90 | 4 | | 22.60 | 24.04 | 2 | Res × Susc |
| 109 | 11 | 10 | 46 | 89 | 99 | | 61.40 | 65.32 | 4 | Res × Susc |
| 110 | 55 | 62 | 71 | 135 | 50 | | 84.00 | 89.36 | 4 | Res × Susc |
| 111 | 75 | 109 | 104 | 37 | 139 | | 88.40 | 94.04 | 4 | Res × Susc |
| 112 | 53 | 87 | 7 | 3 | 7 | | 27.20 | 28.94 | 2 | Res × Susc |
| 113 | 2 | 66 | 3 | 2 | | | 5.75 | 6.12 | 1 | Res × Susc |
| 114 | 2 | 16 | 9 | 6 | 9 | | 8.00 | 8.51 | 1 | Res × Susc |
| 115 | 1 | 14 | 3 | 1 | 1 | | 1.80 | 1.91 | 1 | Res × Susc |
| 116 | 76 | 3 | 61 | 70 | 85 | | 74.40 | 79.15 | 4 | Res × Susc |
| 117 | 0 | 80 | 2 | 1 | 0 | | 1.00 | 1.06 | 1 | Res × Susc |
| 118 | 6 | 2 | 1 | 3 | | | 4.50 | 4.79 | 1 | Res × Susc |
| 119 | 68 | 8 | 58 | | | | 63.33 | 67.38 | 4 | Res × Susc |
| 120 | 14 | 64 | 41 | 100 | 0 | | 31.20 | 33.19 | 3 | Res × Susc |
| 121 | 67 | 1 | 2 | 135 | 5 | | 42.80 | 45.53 | 3 | Res × Susc |
| 122 | 6 | 5 | 2 | 4 | 2 | | 5.20 | 5.53 | 1 | Res × Susc |
| 123 | 17 | 12 | 14 | 8 | 2 | | 11.60 | 12.34 | 2 | Res × Susc |
| 124 | 26 | 17 | 104 | 5 | 67 | | 62.20 | 66.17 | 4 | Res × Susc |
| 125 | 46 | 109 | 98 | 133 | 7 | | 85.00 | 90.43 | 4 | Res × Susc |
| 126 | 94 | 141 | 141 | 8 | 3 | | 51.00 | 54.26 | 3 | Res × Susc |
| 127 | 47 | 9 | 66 | 55 | 2 | | 49.20 | 52.34 | 3 | Res × Susc |
| 128 | 5 | 76 | 111 | 5 | 106 | | 72.80 | 77.45 | 4 | Res × Susc |
| 129 | 109 | 137 | 3 | 0 | 4 | | 25.20 | 26.81 | 2 | Res × Susc |
| 130 | 109 | 10 | 107 | | | | 100.00 | 106.38 | 4 | Res × Susc |
| 131 | 3 | 84 | 77 | 133 | | | 83.00 | 88.30 | 4 | Res × Susc |
| 132 | 131 | 119 | 126 | 154 | 94 | | 121.40 | 129.15 | 4 | Res × Susc |
| 133 | 93 | 102 | 119 | 102 | | | 83.50 | 88.83 | 4 | Res × Susc |
| 134 | 58 | 20 | 96 | 69 | 133 | | 90.20 | 95.96 | 4 | Res × Susc |
| 135 | 107 | 95 | 85 | 55 | 124 | | 85.60 | 91.06 | 4 | Res × Susc |
| 136 | 91 | 57 | 74 | 178 | 64 | 50 | 86.83 | 92.38 | 4 | Res × Susc |
| 137 | 84 | 64 | 116 | 79 | 78 | | 85.60 | 91.06 | 4 | Res × Susc |
| 138 | 87 | 71 | 103 | 113 | | | 78.75 | 83.78 | 4 | Res × Susc |
| 139 | 6 | 12 | 72 | 57 | 49 | | 39.00 | 41.49 | 3 | Res × Susc |
| 140 | 93 | 11 | 115 | 9 | 113 | | 85.80 | 91.28 | 4 | Res × Susc |
| 141 | 68 | 99 | 25 | 6 | 5 | | 34.60 | 36.81 | 3 | Res × Susc |
| 142 | 88 | 69 | 66 | 33 | 98 | | 73.40 | 78.09 | 4 | Res × Susc |
| 143 | 82 | 82 | 15 | 97 | 1 | | 40.00 | 42.55 | 3 | Res × Susc |
| 144 | 91 | 5 | 10 | 126 | 77 | 110 | 79.33 | 84.40 | 4 | Res × Susc |
| 145 | 3 | 62 | 158 | 90 | 33 | | 76.80 | 81.70 | 4 | Res × Susc |
| 146 | 109 | 100 | 136 | 147 | 160 | | 133.60 | 142.13 | 4 | Res × Susc |
| 147 | 85 | 116 | 112 | 139 | 69 | | 105.80 | 112.55 | 4 | Res × Susc |
| 148 | 12 | 124 | 14 | | | | 9.67 | 10.28 | 2 | Res × Susc |
| 149 | 108 | 3 | 78 | 62 | 73 | | 77.80 | 82.77 | 4 | Res × Susc |
| 150 | 53 | 68 | 1 | | | | 50.00 | 53.19 | 3 | Res × Susc |
| 151 | 1 | 96 | 0 | 0 | | | 15.25 | 16.22 | 2 | Res × Susc |
| 152 | 3 | 60 | 2 | 50 | 3 | | 21.40 | 22.77 | 2 | Res × Susc |
| 153 | 105 | 49 | 58 | | | | 88.00 | 93.62 | 4 | Res × Susc |
| 154 | 57 | 101 | 4 | 90 | | | 38.00 | 40.43 | 3 | Res × Susc |
| 155 | 39 | 1 | 49 | | | | 56.33 | 59.93 | 4 | Res × Susc |
| 156 | 103 | 81 | 117 | 83 | | | 103.00 | 109.57 | 4 | Res × Susc |
| 157 | 108 | 109 | 3 | 179 | 105 | | 80.60 | 85.74 | 4 | Res × Susc |
| 158 | 1 | 8 | 50 | | | | 21.33 | 22.70 | 2 | Res × Susc |
| 159 | 57 | 13 | 69 | 4 | 38 | | 35.20 | 37.45 | 3 | Susc × Susc |
| 160 | 55 | 8 | 11 | 71 | 78 | | 48.20 | 51.28 | 3 | Susc × Susc |
| 161 | 8 | 236 | 56 | 12 | | | 44.00 | 46.81 | 3 | Susc × Susc |
| 162 | 43 | 100 | 5 | 69 | 82 | 56 | 56.17 | 59.75 | 3 | Susc × Susc |
| 163 | 41 | 82 | 103 | 84 | 74 | | 78.40 | 83.40 | 4 | Susc × Susc |
| 164 | 79 | 90 | 99 | 57 | 84 | | 78.20 | 83.19 | 4 | Susc × Susc |
| 165 | 52 | 72 | 91 | 60 | 138 | | 86.00 | 91.49 | 4 | Susc × Susc |
| 166 | 141 | 89 | 96 | 95 | 94 | | 103.20 | 109.79 | 4 | Susc × Susc |
| 167 | 0 | 90 | 9 | 31 | 77 | | 32.00 | 34.04 | 3 | Susc × Susc |
| 168 | 91 | 43 | 126 | 135 | | | 116.75 | 124.20 | 4 | Susc × Susc |
| 169 | 64 | 115 | 58 | 74 | | | 87.00 | 92.55 | 4 | Susc × Susc |
| 170 | 105 | 152 | 123 | 162 | 117 | | 127.20 | 135.32 | 4 | Susc × Susc |
| 171 | 136 | 129 | 116 | 53 | | | 96.50 | 102.66 | 4 | Susc × Susc |
| 172 | 90 | 81 | 65 | 4 | | | 53.00 | 56.38 | 3 | Susc × Susc |
| 173 | 0 | 53 | 57 | 141 | | | 72.75 | 77.39 | 4 | Susc × Susc |
| 174 | 88 | 93 | 75 | 48 | 56 | | 71.60 | 76.17 | 4 | Susc × Susc |

TABLE 10-continued

| Entry # | Plant 1 | Plant 2 | Plant 3 | Plant 4 | Plant 5 | Plant 6 | Average Number of Cysts per Plant | FI | SCN Resistance Rating | SCN Pedigree |
|---|---|---|---|---|---|---|---|---|---|---|
| 175 | 59 | 91 | 81 | 85 | 74 | | 69.40 | 73.83 | 4 | Susc × Susc |
| 176 | 3 | 48 | 80 | 0 | 52 | | 34.60 | 36.81 | 3 | Susc × Susc |
| 177 | 92 | 38 | 144 | | | | 95.00 | 101.06 | 4 | Susc × Susc |
| 178 | 0 | 49 | 92 | 51 | 0 | | 29.00 | 30.85 | 3 | Susc × Susc |
| 179 | 34 | 2 | 3 | 39 | 46 | | 33.40 | 35.53 | 3 | Susc × Susc |
| 180 | 5 | 45 | 53 | 2 | | | 34.75 | 36.97 | 3 | Susc × Susc |
| 181 | 84 | 79 | 2 | 72 | | | 59.00 | 62.77 | 4 | Susc × Susc |
| 182 | 103 | 78 | 71 | 53 | | | 87.75 | 93.35 | 4 | Susc × Susc |
| 183 | 30 | 124 | 135 | 84 | 144 | | 102.60 | 109.15 | 4 | Susc × Susc |
| 184 | 37 | 120 | 64 | 55 | 87 | | 66.00 | 70.21 | 4 | Susc × Susc |
| 185 | 40 | 87 | 58 | 79 | 62 | | 53.60 | 57.02 | 3 | Susc × Susc |
| 186 | 104 | 29 | 82 | 97 | 93 | | 83.20 | 88.51 | 4 | Susc × Susc |
| 187 | 127 | 40 | 79 | 77 | 135 | | 99.60 | 105.96 | 4 | Susc × Susc |
| 188 | 66 | 80 | 61 | 66 | 2 | | 51.60 | 54.89 | 3 | Susc × Susc |
| 189 | 59 | 63 | 93 | 70 | 68 | | 75.40 | 80.21 | 4 | Susc × Susc |
| 190 | 2 | 87 | 114 | 99 | 112 | | 68.80 | 73.19 | 4 | Susc × Susc |
| 191 | 117 | 17 | 73 | | | | 113.33 | 120.57 | 4 | Susc × Susc |
| 192 | 56 | 150 | 43 | 107 | | | 51.50 | 54.79 | 3 | Susc × Susc |
| 193 | 61 | 0 | 95 | 55 | 47 | | 93.00 | 98.94 | 4 | Susc × Susc |
| 194 | 127 | 207 | 119 | 89 | 91 | | 105.00 | 111.70 | 4 | Susc × Susc |
| 195 | 57 | 99 | 84 | 143 | 96 | | 95.00 | 101.06 | 4 | Susc × Susc |
| 196 | 53 | 95 | 63 | 66 | | | 60.25 | 64.10 | 4 | Susc × Susc |
| 197 | 26 | 59 | 53 | 86 | 26 | | 56.80 | 60.43 | 4 | Susc × Susc |
| 198 | 56 | 93 | 90 | 35 | 90 | | 69.20 | 73.62 | 4 | Susc × Susc |
| 199 | 103 | 75 | 65 | 52 | | | 70.50 | 75.00 | 4 | Susc × Susc |
| 200 | 101 | 62 | 77 | 62 | 103 | | 96.40 | 102.55 | 4 | Susc × Susc |
| 201 | 107 | 139 | 40 | 123 | 49 | | 86.80 | 92.34 | 4 | Susc × Susc |
| 202 | 19 | 115 | 42 | 75 | 73 | | 49.60 | 52.77 | 3 | Susc × Susc |
| 203 | 43 | 39 | 44 | 29 | | | 43.75 | 46.54 | 3 | Susc × Susc |
| 204 | 3 | 59 | 51 | 66 | 3 | | 38.40 | 40.85 | 3 | Susc × Susc |
| 205 | 62 | 69 | 49 | 50 | | | 57.00 | 60.64 | 4 | Susc × Susc |
| 206 | 74 | 67 | 47 | 60 | 65 | | 63.00 | 67.02 | 4 | Susc × Susc |
| 207 | 94 | 69 | 73 | 0 | 0 | | 52.60 | 55.96 | 3 | Susc × Susc |
| 208 | 67 | 96 | 29 | 24 | 1 | | 39.00 | 41.49 | 3 | Susc × Susc |
| 209 | 75 | 74 | 44 | 86 | 75 | | 56.20 | 59.79 | 3 | Susc × Susc |
| 210 | 84 | 1 | 8 | 47 | 79 | | 44.00 | 46.81 | 3 | Susc × Susc |
| 211 | 8 | 2 | 45 | 43 | 3 | | 36.20 | 38.51 | 3 | Susc × Susc |
| 212 | 4 | 82 | 94 | 8 | 122 | | 46.80 | 49.79 | 3 | Susc × Susc |
| 213 | 60 | 6 | 4 | 12 | | | 21.22 | 22.61 | 2 | Susc × Susc |
| 214 | 12 | 9 | 3 | 8 | 15 | | 10.00 | 10.64 | 2 | Susc × Susc |
| 215 | 20 | 12 | 8 | 1 | 2 | | 9.00 | 9.57 | 1 | Check | A3559 |
| 216 | 60 | 14 | 74 | 57 | 60 | | 74.00 | 78.72 | 4 | Check | Macon |
| 217 | 3 | 119 | 2 | 1 | 3 | | 2.40 | 2.55 | 1 | Check | NIL Res |
| 218 | 87 | 3 | 58 | 120 | 87 | | 95.40 | 101.49 | 4 | Check | NIL Sus |
| 219 | 121 | 125 | 77 | 96 | | | 94.00 | 100.00 | 4 | Check | Essex |
| 220 | 80 | 82 | 103 | 119 | 76 | | 99.40 | 105.32 | 4 | Check | Hamilton |
| 221 | 3 | 117 | 0 | 0 | 0 | | 0.80 | 0.85 | 1 | Check | PI90763 |
| 222 | 5 | 1 | 4 | 2 | | | 4.25 | 4.52 | 1 | Check | PI88788 |
| 223 | 0 | 6 | 2 | 1 | 0 | | 1.00 | 1.06 | 1 | Check | Peking |
| 224 | 2 | 2 | 2 | 0 | 0 | | 1.40 | 1.49 | 1 | Check | Pickett 71 |
| 225 | 135 | 3 | 138 | 172 | 126 | | 154.00 | 163.83 | 4 | Check | Hutcheson |
| 226 | 1 | 199 | 0 | 1 | 0 | | 0.80 | 0.85 | 1 | Check | PI89772 |
| 227 | 1 | 2 | 0 | 4 | 30 | | 8.20 | 8.72 | 1 | Check | PI438489B |
| 228 | 0 | 6 | 2 | 1 | 1 | | 1.80 | 1.91 | 1 | Check | PI404166 |
| 229 | 0 | 5 | 0 | 1 | | | 0.75 | 0.80 | 1 | Check | PI437654 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

REFERENCES

Bewig, K. M. 1992. Discriminate analysis of vegetable oils using near infrared reflectance spectroscopy. M.Sc. Thesis. University of Missouri-Columbia.

Brim, J. P. and B. R. Ross. 1966. Registration of Pickett soybeans. Crop Science. 6:305.

Buss, G. R., H. M. Camper, Jr., and C. W. Roane. 1988. Registration of 'Hutcheson' soybean. Crop Science. 28:1024-1025.

Delwiche, S. R., R. A. Graybosch, and C. J. Peterson. 1999. Identification of wheat lines possessing the 1AL.1RS or 1BL.1RS wheat-rye translocation by near-infrared reflectance spectroscopy. Cereal Chemistry. 76:255-260.

Dyer, D. J., and P. Feng. 1995. NIR applications in the development of genetically altered grains. In Proc. 7th Int. Conf. On Near-Infared Spectroscopy. Aug. 6-11, 1995. Montreal, Canada. NIR Publications, West Sussex, UK.

Endo, B. Y. 1964. Penetration and development of Heterodera glycines in soybean roots and related anatomical changes. Phytopathology 5:79-88.

Epps, J. M., and A. Y. Chambers. 1962. The soybean cyst nematode symptoms, life cycle, spread, host range, resistance and control. *Tennessee Farm Home Sci.* 41:13-16.

Golden, A. M., J. M. Epps, R. D. Riggs, L. D. Duclos, J. A. Fox, and R. L. Bernard. 1970. Terminology and identity of infraspecific forms of the soybean cyst nematode (*Heterdera glycines*). *Plant Disease Reporter.* 54:544-546.

Hymowitz, T. 1970. On the domestication of the soybean. *Economic Botany* 24:408-421.

Nickell, C. D., D. J. Thomas, T. R. Cary, and D. Heavner. 1996. Registration of 'Macon' soybean. *Crop Science.* 36:1410:

Nickell, C. D., D. J. Thomas, and P. Stephens. 1990. Registration of 'Hamilton' soybean. *Crop Science.* 30:1364.

Nilsson, N., T. Ehmqvist, and U. Carlsson. 1994. Use of near-infrared reflectance spectroscopy and multivariate data analysis to detect anther smut disease (*Microbotryum violacem*) in *Silene dioica*. *Pytopathology.* 84:764-770.

Osborne, B. G. and T. Fearn. 1986. *Near Infrared Spectroscopy in Food Analysis*. John Wiley & Sons Inc. New York, N.Y.

Qiu, J., J. Hamann, N. Koka-Burelle, D. B. Weaver, R. Rodreguez-Kabana and S. Tuzun. 1997. Activity and differential induction of chitinase isozymes in soybean cultivars resistant or susceptible to root-knot nematodes. *Journal of Nematology.* 29:523-530.

Rao Arelli, A. P., J. A. Wrather, and S. C. Anand. 1991. A rapid method for inoculating soybean seedlings with *Heterdera glycines*. *Plant Disease.* 75:594-595.

Roberts, C. A., K. J. Moore, D. W. Graffis, H. W. Kirby, and R. P. Walgenbach. 1987. Quantification of mold in hay by near infrared reflectance spectroscopy. *Journal of Dairy Science.* 70:2560-2564.

Roberts, C. A., R. E. Joost and G. E. Rottinghaus. 1997. Quantification of ergovaline in tall fescue by near infrared reflectance spectroscopy. *Crop Science.* 37:281-284.

Ross, J. P. 1962. Physiological strains of *Heterdera glycines*. *Plant Disease Reporter* 46:766-769.

Riggs, R. D. 1977. Worldwide distribution of soybean cyst nematode and its economic importance. *Journal of Nematology* 9:34-39.

Riggs, R. D., and D. P. Schmitt. 1988. Complete characterization of the race scheme for *Heterdera glycines*. *Journal of Nematology* 20:392-395.

Rutherford, R. S., 1998. Prediction of resistance in sugarcane to stalk borer *Eldana saccharina* by near-infrared spectroscopy on crude budscale extracts: involvement of chlorogenates and flavonoids. *Journal of Chemical Ecology.* 24:1447-1463.

Schapaugh, W. T., P. A. Owen, K. M. Clark, and D. A. Sleper. 1998. Registration of 'Magellan' soybean. *Crop Science.* 38:892.

Schmitt D. P., and G. Shannon. 1992. Differentiating soybean responses to *Heterodera glycines* races. *Crop Science.* 32:275-277.

Winstead W. W., C. B. Skotland, and J. W. Sasser. 1955. Soybean cyst nematode in North Carolina. *Plant Disease Reporter* 39:9-11.

Yue, P. 2000. Genetics of Resistance to SCN Races in Soybean. Ph. D. Thesis. University of Missouri-Columbia.

What is claimed is:

1. A method for predicting the resistance of a soybean seed to a soybean cyst nematode (SCN) comprising steps of:
   (a) analyzing a soybean seed sample using a near-infrared (NIR) spectrometer to produce assay spectral data, wherein the soybean seed sample has unknown resistance to SCN;
   (b) analyzing at least one reference soybean seed using a NIR spectrometer to produce reference spectral data, wherein the reference seed has a known SCN resistant genotype or SCN susceptible genotype;
   (c) comparing NIR peak intensities of the assay spectral data and reference spectral data using discriminant analysis; and
   (d) classifying the soybean seed sample as SCN resistant or SCN susceptible based on said discriminate analysis.

2. An electronically programmable apparatus for predicting the resistance of a soybean seed to a soybean cyst nematode (SCN) comprising:
   (a) a near-infrared (NIR) spectrophotometer configured to analyze (i) a soybean seed sample with unknown resistance to SCN to produce assay spectral data; and (ii) at least one reference soybean seed having a known SCN resistant genotype or SCN susceptible genotype to produce reference spectral data; and
   (b) machine readable code comprising executable machine readable instructions for (i) comparing, using a discriminant analysis model, NIR peak intensities of the assay spectral data and reference spectral data from the analyzed soybean seed sample and reference seed(s), and (ii) classifying the soybean seed sample as SCN resistant or SCN susceptible based on said discriminate analysis.

* * * * *